United States Patent
Murray et al.

(10) Patent No.: US 11,801,349 B2
(45) Date of Patent: Oct. 31, 2023

(54) TELESCOPING PLUNGER ROD

(71) Applicants: Fresenius Kabi USA, LLC, Lake Zurich, IL (US); Fresenius Kabi Austria GmbH, Graz (AT)

(72) Inventors: Christopher J. Murray, Lake Zurich, IL (US); Kurt Attermeier, Lake Zurich, IL (US); Christoph Zauner, Graz (AT)

(73) Assignees: Fresenius Kabi USA, LLC, Lake Zurich, IL (US); Fresenius Kabi Austria GmbH, Graz (AT)

( * ) Notice: Subject to any disclaimer, the term of this patent is extended or adjusted under 35 U.S.C. 154(b) by 218 days.

(21) Appl. No.: 17/242,085

(22) Filed: Apr. 27, 2021

(65) Prior Publication Data
US 2022/0339362 A1    Oct. 27, 2022

(51) Int. Cl.
*A61M 5/315* (2006.01)

(52) U.S. Cl.
CPC ...... *A61M 5/3158* (2013.01); *A61M 5/31511* (2013.01); *A61M 2005/3151* (2013.01); *A61M 2202/0007* (2013.01)

(58) Field of Classification Search
CPC .............. A61M 5/315; A61M 5/31501; A61M 5/31511; A61M 5/31515; A61M 2005/31508; A61M 2005/31518; A61M 2005/31506
See application file for complete search history.

(56) References Cited

U.S. PATENT DOCUMENTS

| | | | |
|---|---|---|---|
| 7,976,510 B2 | 7/2011 | Janish et al. | |
| 8,172,813 B2 | 5/2012 | Janish | |
| 8,801,675 B2 | 8/2014 | Janish et al. | |
| 10,159,796 B2 | 12/2018 | Schiff et al. | |
| 10,960,139 B2 | 3/2021 | Schiff et al. | |
| 11,452,818 B2 | 9/2022 | Schiff et al. | |
| 2010/0228200 A1 | 9/2010 | Moed | |
| 2011/0196313 A1* | 8/2011 | Mudd | A61M 5/31511 604/219 |
| 2011/0264051 A1* | 10/2011 | Janish | A61M 5/3158 604/208 |

FOREIGN PATENT DOCUMENTS

| | | |
|---|---|---|
| WO | 2013048864 A2 | 4/2013 |
| WO | 2013048867 A1 | 4/2013 |
| WO | 2020168412 A1 | 8/2020 |

* cited by examiner

*Primary Examiner* — Nathan R Price
*Assistant Examiner* — Justin L Zamory
(74) *Attorney, Agent, or Firm* — BLANK ROME LLP

(57) ABSTRACT

Devices and methods for use with syringes are disclosed. A plunger rod includes an outer housing having proximal and distal ends and a lumen between the ends, as well as an inner body axially slidable within the lumen between a first and second position. The inner body has a retention member extending therefrom. When the inner body is in the first position, the plunger rod has a first length, and, when the inner body is in the second position, the plunger rod has a second length greater than the first length. When the inner body is in the second position, the inner body is configured to be rotated relative to the outer housing until the retention member is received within the outer housing to preclude the inner body from moving in the axial direction.

27 Claims, 27 Drawing Sheets

TELESCOPING PLUNGER ROD

TECHNICAL FIELD

This disclosure generally relates to devices and methods of dispensing materials from syringes, and more particularly relates to an adjustable plunger rod for use with syringes.

BACKGROUND

Syringe assemblies are used to hold, transport, and deliver liquids. For example, syringes are often utilized in medical environments to administer one or more medicinal liquids. Syringe assemblies may differ in size, and their specific dimensions are dictated by the desired application and the specific liquid to be administered. In some instances, syringes may be pre-filled with one or more liquids that are then dispensed from the syringe and combined with other elements.

Clinicians and medical professionals can administer liquids to patients from prepared syringes that are pre-filled with a desired medicament or diagnostic. Such pre-filled syringes allow the clinician to administer the medicament or diagnostic efficiently without the need to prepare and fill the syringe with the desired amount of medicament or diagnostic. The pre-filled syringes can be prepared and filled prior to the clinicians' receiving them, and as such, the packaging, transportation, and storage of the pre-filled syringes becomes important.

When a syringe is filled with liquid, a plunger rod is commonly inserted into the syringe upon filling and packaging. The plunger rod can remain in the syringe, and the clinician can then use the pre-filled syringe by depressing the plunger rod. As such, the combination of the syringe and plunger rod can have a large footprint. In other scenarios, the syringe can be pre-filled, but the plunger rod can be packaged separately from the pre-filled syringe. This results in a smaller footprint, but requires the clinician to assembly the plunger rod with the syringe prior to administering the liquid, which decreases efficiency and introduces possible error.

Accordingly, there is a need for a pre-filled syringe assembly that is both compact and ready-to-use to improve efficiency and safety.

SUMMARY

The foregoing needs are met by various aspects of syringe assemblies and plunger rod assemblies disclosed. According to an aspect of the disclosure, a plunger rod for use with a syringe includes an outer housing having a proximal end and a distal end opposite the proximal end, and further defining a lumen between the proximal end and the distal end. The plunger rod also includes an inner body configured to be movable within the lumen between a first position and a second position along an axial direction. The inner body comprises a retention member extending from the inner body in a direction angularly offset from the axial direction. When the inner body is in the first position relative to the outer housing, the plunger rod has a first length, and, when the inner body is in the second position relative to the outer housing, the plunger rod has a second length greater than the first length. When the inner body is in the second position relative to the outer housing, the inner body is configured to be rotated relative to the outer housing until the retention member is received within the outer housing to preclude the inner body from moving in the axial direction towards the first position.

Optionally, the outer housing may define a plurality of channels that are spaced in the axial direction. Each of the plurality of channels may be configured to receive the retention member. Optionally, the plurality of channels may include a distal channel and an intermediate channel adjacent the distal channel. The retention member may be configured to be received into the distal channel when the inner body is in the first position relative to the outer housing, and the retention member may be configured to be received into the intermediate channel when the inner body is in the second position relative to the outer housing.

Optionally, when the retention member is disposed in the distal channel and not in the intermediate channel, the retention member may be configured to contact the outer housing such that the inner body is precluded from being rotated relative to the outer housing.

Optionally, when the retention member is received in the intermediate channel, the inner body may be rotatable relative to the outer housing.

Optionally, the plunger rod may include a proximal channel spaced from the distal channel and configured to receive the retention member therein. When the retention member is received in the proximal channel but not in the intermediate channel, the retention member may be configured to contact the outer housing such that the inner body is precluded from being rotated relative to the outer housing. The intermediate channel may be disposed between the proximal channel and the distal channel.

Optionally, the distal channel may be tapered in the axial direction towards the distal end of the outer housing. Optionally, the outer housing may define a contact surface in communication with the lumen. The contact surface may be configured to be placed into contact with a face defined on the inner body when the inner body is rotated relative to the outer housing while the inner body is in the second position.

Optionally, the face of the inner body and the contact surface of the outer housing may be in a friction fit when the face is in contact with the contact surface to resist relative rotation between the inner body and the outer housing to move the face out of contact with the contact surface.

Optionally, the contact surface may include a retention member contact surface and an inner body contact surface. The face of the inner body may be defined by the distal end of the inner body and by the retention member. The retention member contact surface may be configured to contact the portion of the face defined by the retention member, and the inner body contact surface may be configured to contact the portion of the face defined by the inner body that does not define the retention member.

Optionally, when the inner body is in the second position, the inner body may be configured to receive an axial force applied thereto and to transfer the axial force therefrom to the outer housing via the contact between the face of the inner body and the contact surface of the outer housing.

Optionally, the contact surface may include a lower contact surface and an upper contact surface spaced from the lower contact surface. The retention member of the inner body may be configured to be received into a space defined between the upper contact surface and the lower contact surface and to be in friction fit with the upper contact surface and the lower contact surface.

Optionally, one of the contact surface and the face of the inner body may define a notch thereon, and the other of the contact surface and the face may define a protrusion thereon.

When the inner body is rotated relative to the outer housing while the inner body is in the second position, the protrusion may be receivable in the notch. Optionally, rotation of the inner body relative to the outer housing in a first rotational direction may cause the protrusion to be moved into the notch, such that the protrusion is configured to contact at least one wall of the notch to preclude rotation of the inner body relative to the outer housing in a second rotational direction opposite the first rotational direction. Optionally, the protrusion may be disposed on the face, and the notch is disposed on the contact surface of the outer housing. Optionally, the plunger rod may further include a plurality of the protrusions and a plurality of the notches, and the plurality of protrusions may be the same as the plurality of notches.

Optionally, the retention member may include a base extending from the inner body and a protrusion extending from the base. The protrusion may be configured to be deformed by application of a force, and resiliently undeforms upon removal of the force. Optionally, the outer housing may define a detent extending into the lumen that is configured to be contacted by the retention member. Upon contact with the detent, the protrusion may be configured to deform due to the contact and due to application of the force, such that the retention member is moved past the detent. The protrusion may return to its original configuration when the protrusion is moved past the detent. Optionally, the plunger rod may further include a plunger disposed adjacent to the distal end of the outer housing, such that the plunger may be configured to contact a liquid within the syringe to cause dispensing thereof from the syringe.

According to another aspect of the disclosure, a syringe assembly includes a syringe configured to receive a liquid therein and a plunger rod configured to be slidably received within the syringe. The plunger rod includes an outer housing, an inner body, and a plunger disposed on the outer housing. The outer housing has a proximal end and a distal end opposite the proximal end, and further defines a lumen between the proximal end and the distal end. The inner body is configured to be movable within the lumen between a first position and a second position along an axial direction. The inner body includes a retention member extending from the inner body in a direction angularly offset from the axial direction. When the inner body is in the first position relative to the outer housing, the plunger rod has a first length, and when the inner body is in the second position relative to the outer housing, the plunger rod has a second length greater than the first length. When the inner body is in the second position, the inner body is configured to be rotated relative to the outer housing until the retention member is received within the outer housing to preclude the inner body from moving in the axial direction towards the first position.

According to another aspect, a pharmaceutical product may include a syringe assembly as described above. The liquid may include an active ingredient selected from a therapeutic agent, a diagnostic agent, a nutrient, and a combination thereof.

Optionally, the active ingredient may be selected from the group consisting of an opioid, benzodiazepine, α2-adrenergic receptor agonist, beta blocker, morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, and hydroxyprogesterone.

According to another aspect, a method of using a plunger rod is disclosed. The plunger rod includes an outer housing and an inner body slidably and rotationally receivable within the outer housing. The plunger rod has a proximal end and a distal end spaced from the proximal end along an axial direction. The method includes moving the inner body relative to the outer housing in the axial direction away from the proximal end to expand the plunger rod to an extended configuration, rotating the inner body relative to the outer housing to lock the inner body to the outer housing, and applying an axial force to the plunger rod to cause the plunger rod to move relative to a syringe barrel to cause dispensing of a liquid from the syringe barrel.

Optionally, the plunger rod may have a first length measured between the proximal end and the distal end when in the compact configuration, and a second length greater than the first length measured between the proximal and distal ends when the plunger rod is in the extended configuration. Optionally, the outer housing may include a contact surface, and the inner body may include a face, where rotating the inner body relative to the outer housing may include axially aligning the contact surface with the face such that the contact surface and the face are configured to contact each other to preclude axial movement of the inner body relative to the outer housing.

Optionally, the method may further include inserting the plunger rod into the syringe barrel, such that the plunger rod is configured to be slidably moved within the syringe barrel. Optionally, the method may further include, prior to expanding the plunger rod to the extended configuration, inserting the inner body into the outer housing.

BRIEF DESCRIPTION OF THE DRAWINGS

The present application is further understood when read in conjunction with the appended drawings. For the purpose of illustrating the subject matter, the drawings depict exemplary aspects of the subject matter; however, the presently disclosed subject matter is not limited to the specific methods, devices, and systems disclosed. In the drawings.

Aspects of the disclosure will now be described in detail with reference to the drawings, wherein like reference numbers refer to like elements throughout, unless specified otherwise.

DETAILED DESCRIPTION

A syringe can be used to administer a liquid to a patient. The liquid can be a pharmaceutical formulation comprising an active ingredient and, optionally, one or more excipients. The syringe can be pre-filled to have a desired and fixed quantity of a specific active ingredient or mix of active ingredients. The clinician can then use the pre-filled syringe to administer its contents to the patient.

Figure 1:
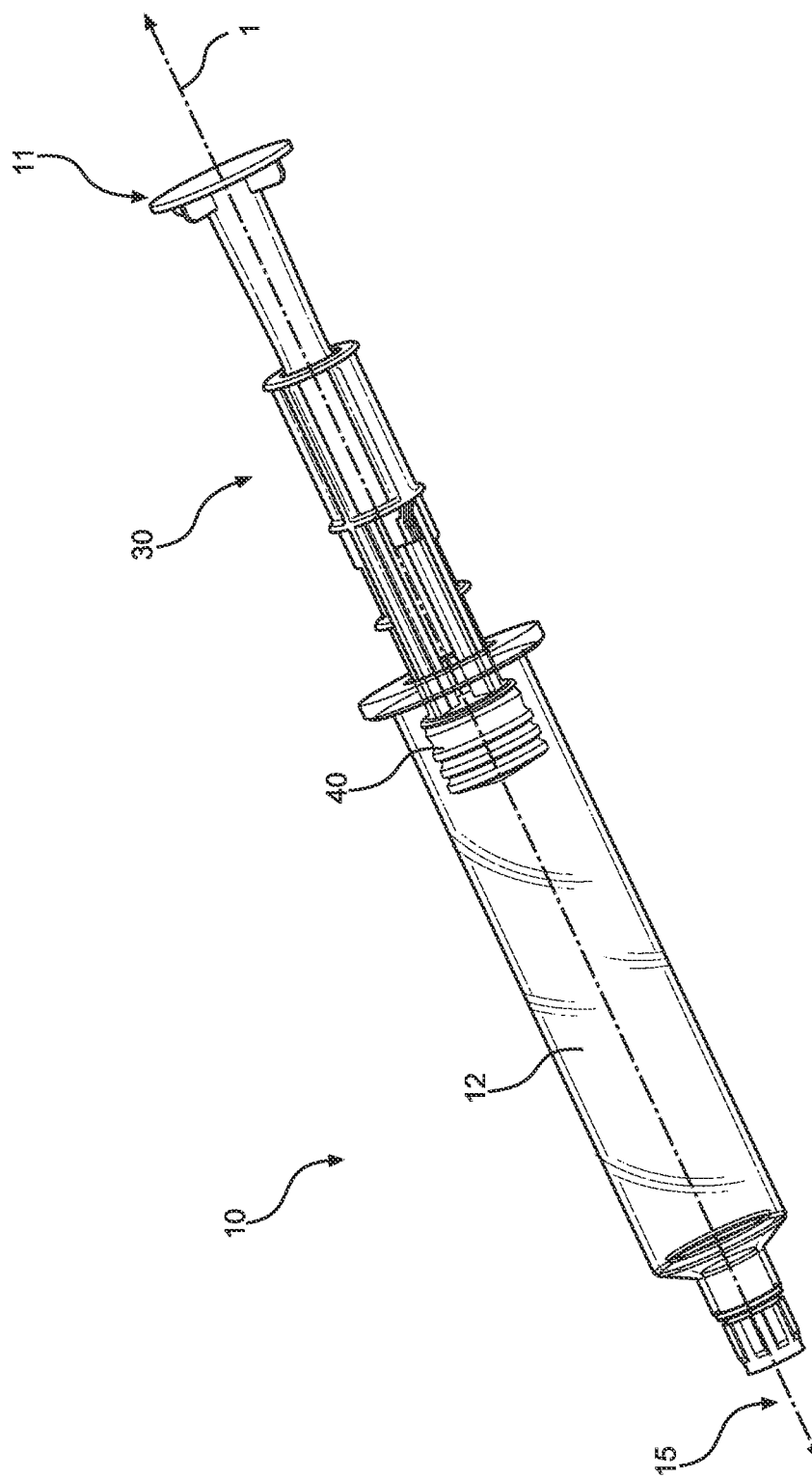
FIG. 1 illustrates a side perspective view of a syringe assembly.

As shown in FIG. 1 for example, disclosed herein are syringe assemblies 10, as well as methods of using such assemblies, that include a pre-filled syringe 12 and a plunger rod 30 operatively connected to the syringe 12. The plunger rod 30 is configurable between at least a compact configuration and an extended configuration. This allows for the plunger rod 30 and the pre-filled syringe 12 to be stored together, in a connected configuration, without requiring as much physical storage space as required by existing traditional one-piece plunger rods. The syringe assembly 10 extends between a proximal end 11 and a distal end 15 spaced from the proximal end 11 along an axis 1. The specific arrangement of components that comprise the syringe assembly 10 is described below.

Figure 2:
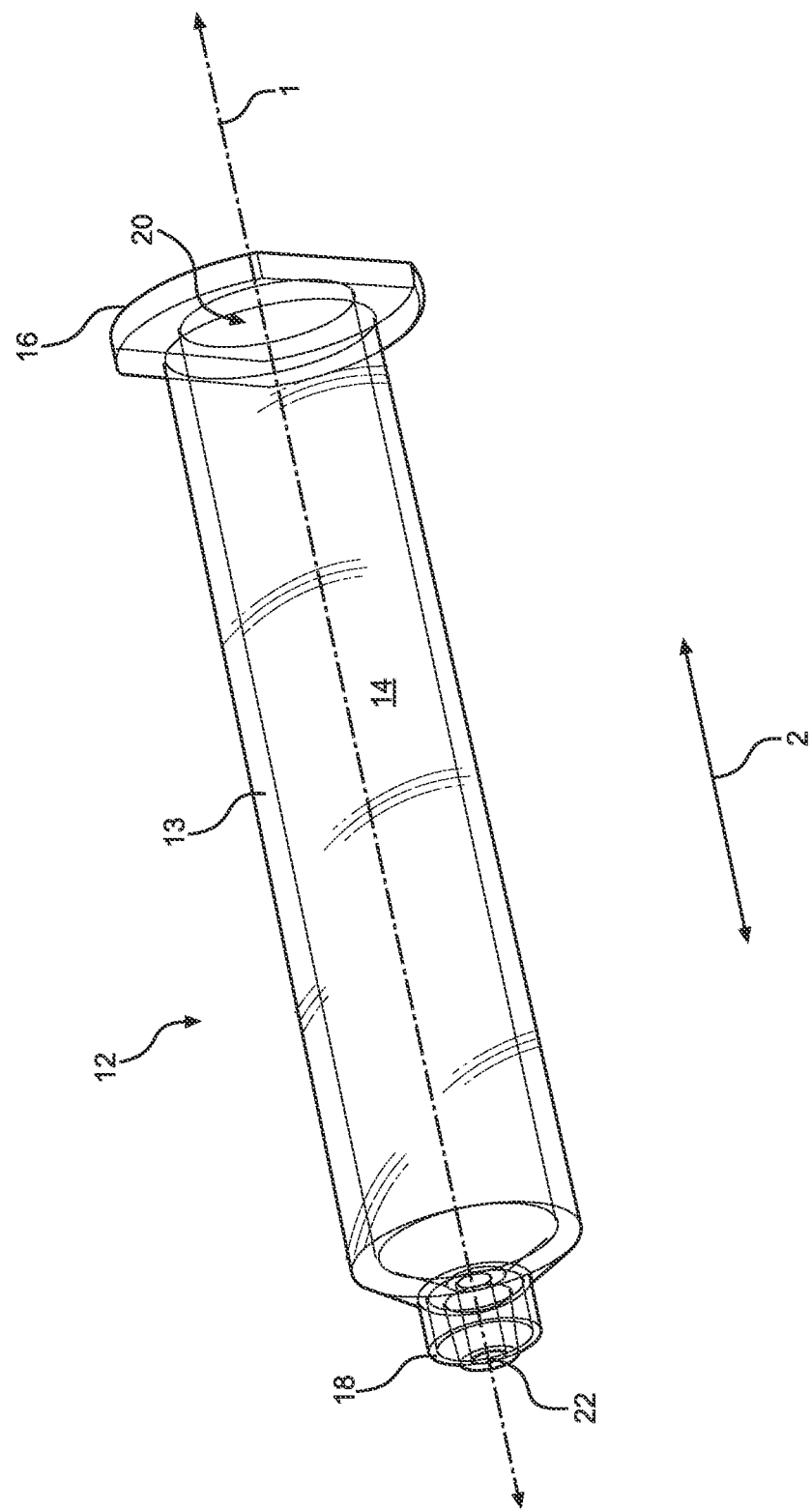
FIG. 2 illustrates a perspective view of a syringe.

Referring to FIGS. 1 and 2, the syringe 12 includes a body, or barrel, 13 that extends between a proximal end 16 and a distal end 18. The syringe barrel 13 may be substantially cylindrical and may be at least partly hollow to define a chamber 14 therein. A proximal opening 20 is defined at the proximal end 16 of the syringe barrel 13, and a distal opening 22 is defined at the distal end 18 of the syringe barrel 13. The chamber 14 is in fluid communication with both the proximal opening 20 and the distal opening 22. Liquid may be introduced into the chamber 14 through either the proximal opening 20 or the distal opening 22.

The syringe 12 can include a plastic or glass material and can be formed via molding or other commonly used manufacturing process. In some aspects, the syringe 12 can include cyclic olefin copolymer (COC), cyclic olefin polymer (COP), glass, or various other materials. The syringe barrel 13 may include a substantially transparent material, such that a user of the syringe assembly 10 can monitor the material levels within the syringe barrel 13. Although the syringe barrel 13 is depicted as being substantially cylindrical, the present disclosure is not intended to be limited to a particular shape or cross section.

The distal end 18 may be configured to connect to an external component, such as a needle, tube, or other medical connector (not shown). In some aspects, the distal end 18 may include a Luer connection.

The proximal opening 20 is sized to receive a plunger rod 30 therein. It will be appreciated that the syringe 12 should be dimensioned such that the plunger rod 30 can slidably move into and within the chamber 14, while simultaneously precluding the liquid from leaking out of the proximal opening 20. One or more seals can be disposed on the syringe 12, on the plunger rod 30, or on both, to reduce the likelihood of leaks. As shown in FIG. 1, for example, a plunger 40 can be slidably positioned within the chamber 14 of the syringe barrel 13 and be slidably movable within the chamber 14. The plunger 40 may be disposed on the plunger rod 30, for example being attached to a plunger retention member 42 (shown in FIG. 4). It will be appreciated that the liquid in the chamber 14 would thus be disposed between the plunger 40 and the distal end 18 of the syringe barrel 13.

As the plunger 40 is moved along an insertion axis 1 towards the distal end 18, the plunger 40 contacts the liquid in the chamber 14 and forces the liquid to move towards and out through the distal opening 22 of the syringe barrel 13. Alternatively, as the plunger 40 moves proximally toward the proximal end 16 along the insertion axis 1, the plunger 40 can function to draw material into the chamber 14 through the distal opening 22. For purposes of this disclosure, an axial direction 2 is defined as being parallel to the insertion axis 1. The axial direction 2 can refer to a either direction along the insertion axis 1, for example, towards the proximal end 16 and towards the distal end 18. Throughout this disclosure, a "distal" direction, or movement "distally" in relation to a described component, can refer to movement along the axial direction 2 generally towards the distal end 15 of the syringe assembly 10. Conversely, a "proximal" direction, or movement "proximally" in relation to a described component, can refer to movement along the axial direction 2 generally towards the proximal end 11 of the syringe assembly 10 and in the opposite direction of the distal direction.

The plunger 40 is configured to define the proximal-most extent to which the liquid within the chamber 14 can travel within the chamber 14. The plunger 40 can have a substantially cylindrical body, although the shape of the plunger body can generally conform to the cross-sectional shape of the chamber 14. The plunger 40 can include a substantially flexible material, such as rubber. The flexibility of the material allows the plunger 40 to act as a seal within the chamber 14, such that the liquid within the chamber 14 cannot move past the plunger 40 towards the proximal end 16 of the syringe barrel 13.

Figure 3:
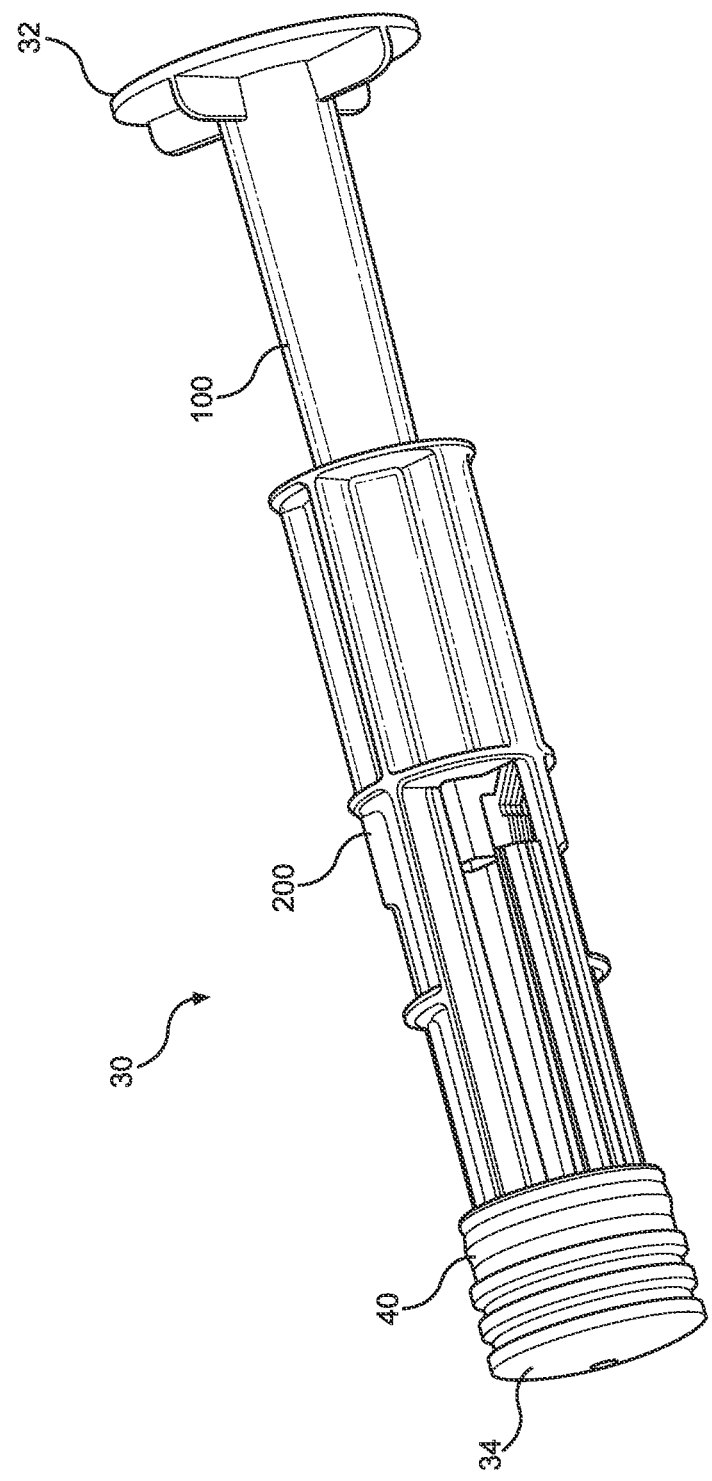
FIG. 3 illustrates a side perspective view of a plunger rod.
Figure 4:
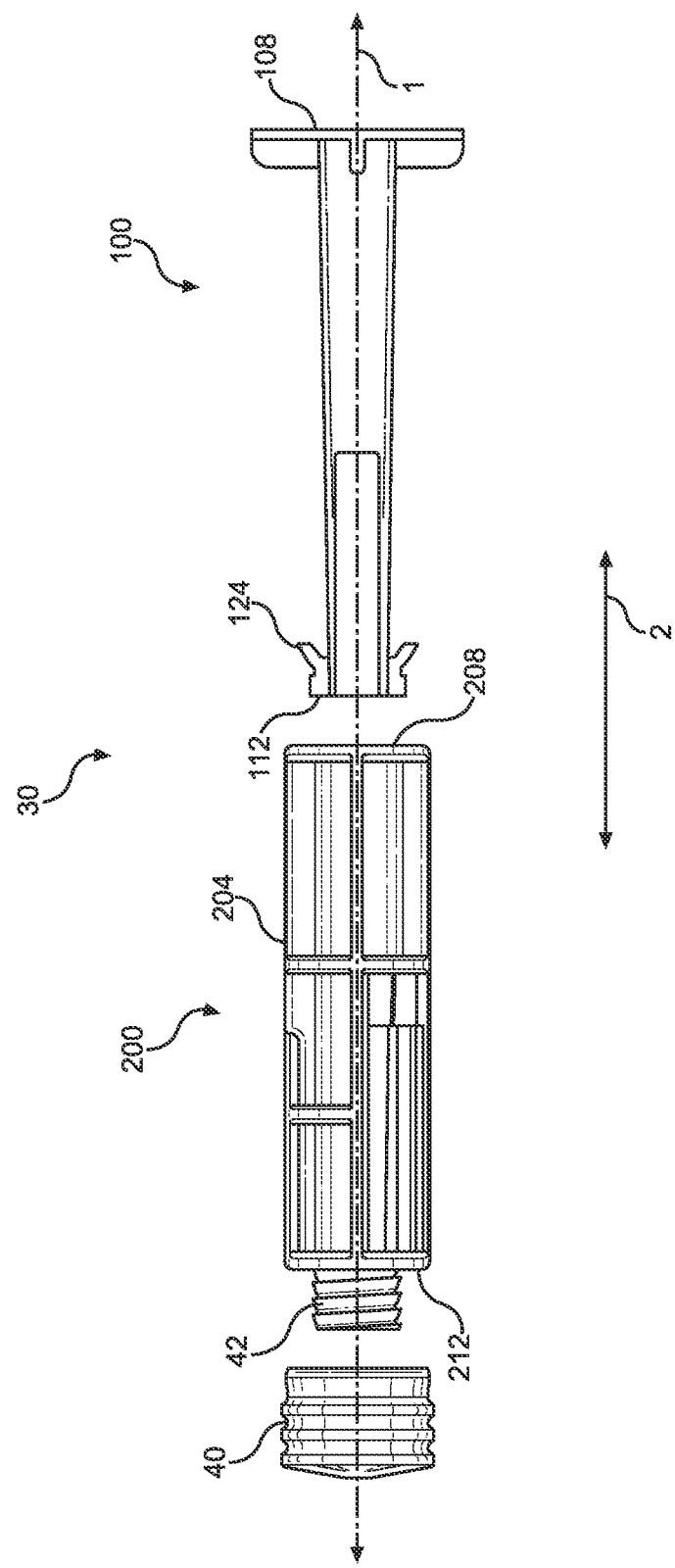
FIG. 4 illustrates a side perspective of an exploded view of the plunger rod of FIG. 3.

The syringe 12 is configured to receive therein a plunger rod 30. At least a portion of the plunger rod 30 is received through the proximal opening 20 of the syringe barrel 13. The plunger rod 30 is configured to move slidably within the chamber 14 between the proximal end 16 and the distal end 18 of the syringe barrel 13 along the insertion axis 1 along the axial direction 2. Referring to FIGS. 3 and 4, the plunger rod 30 includes a proximal end 32 and a distal end 34 spaced from the proximal end 32 along the axial direction 2. The plunger rod 30 includes an inner body 100 and an outer housing 200. The outer housing 200 is configured to slidably and rotationally receive the inner body 100 therein, as will be described in detail below.

Referring to FIGS. 4-8, the inner body 100 extends between a proximal end 108 and a distal end 112 spaced from the proximal end 108 along the axial direction 2. The inner body 100 may include a substantially cylindrical portion between the proximal and distal ends 108, 112. In some aspects, the inner body 100 may include a non-cylindrical portion. In some aspects, the inner body 100 may be tapered from the proximal end 108 to the distal end 112. That is, the inner body 100 may define a first cross-sectional dimension 136A on one portion thereof and a second cross-sectional dimension 136B, that is different from the first cross-sectional dimension 136A, on another portion thereof (see, e.g. FIG. 6). The first cross-sectional dimension 136A may be greater than the second cross-sectional dimension 136B. In some aspects, the first cross-sectional dimension 136A may be closer to the proximal end 108 of the inner body 100 than the second cross-sectional dimension 136B. It will be appreciated that the specific measurements of the inner body 100 will depend on complimentary measurements of other components described throughout this application, as well as on the desired use of the syringe assembly 10.

A handle 116 may be disposed on the inner body 100, for example, adjacent the proximal end 108. A user may grip or otherwise contact the handle 116 to cause the inner body 100 to move along the insertion axis 1. The user can push or pull on the handle 116 to selectively cause the inner body 100 to move towards or away from the distal end 34 of the plunger rod 30, respectively. When then user applies force to the handle 116 in a first direction (e.g. towards the distal end 34 of the plunger rod 30), the plunger rod 30 can cause dispensing of the material within the syringe 12. Although the handle 116 is depicted as substantially circular in shape, it will be appreciated that the handle 116 may include another suitable shape.

Figure 5:
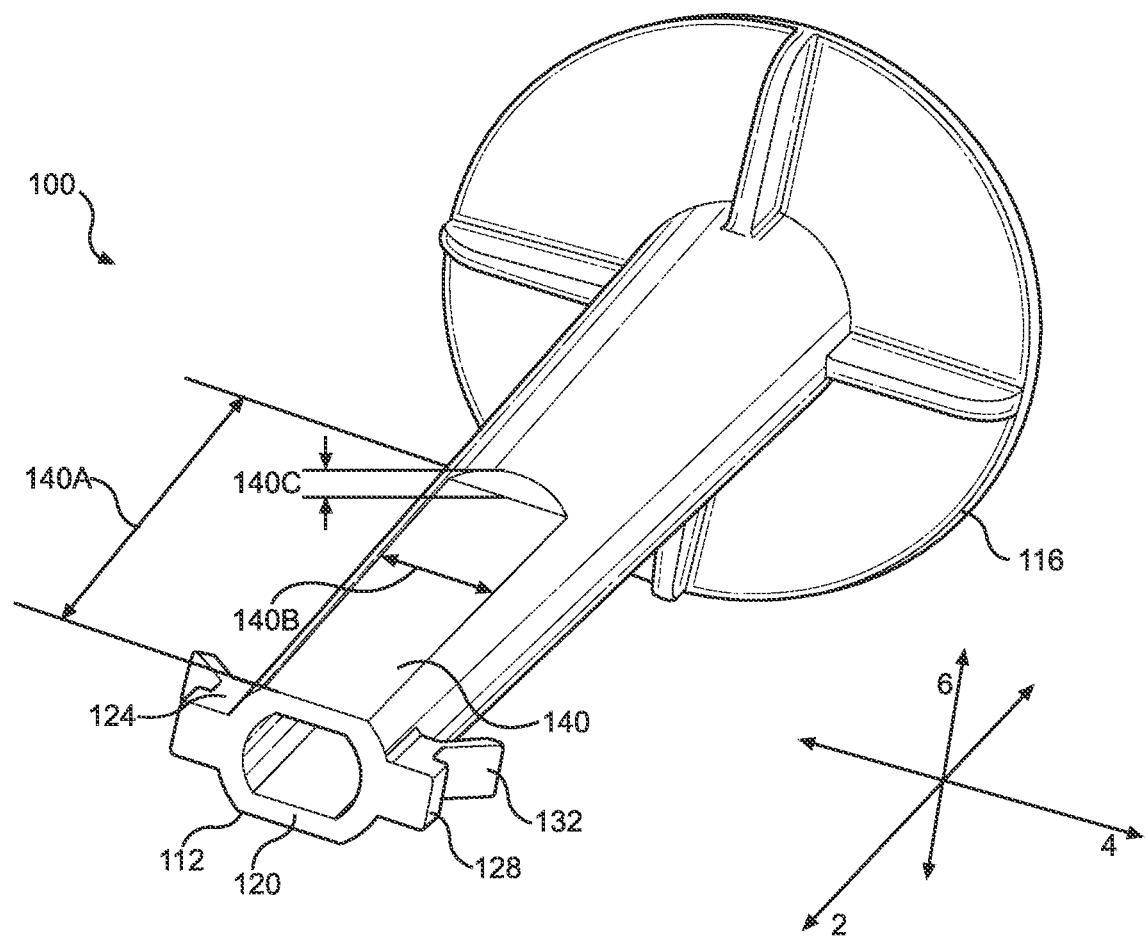
FIG. 5 illustrates an angled perspective view of an inner body of the plunger rod.
Figure 6:
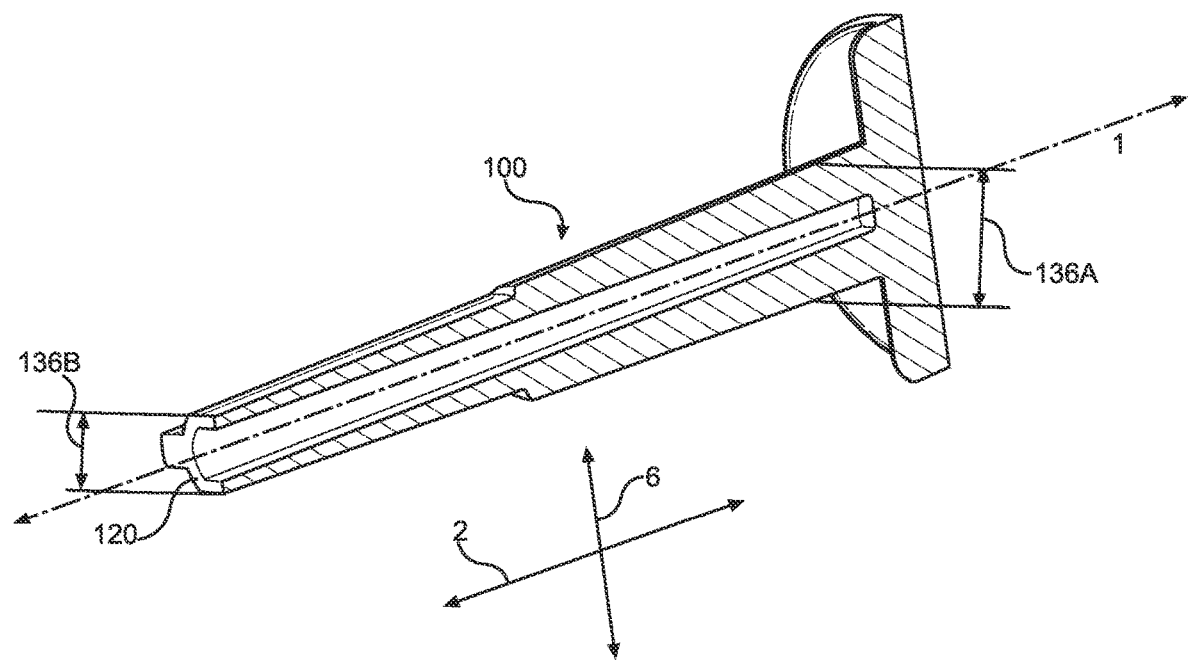
FIG. 6 illustrates a side cross-sectional view of the inner body of FIG. 5.
Figure 7:
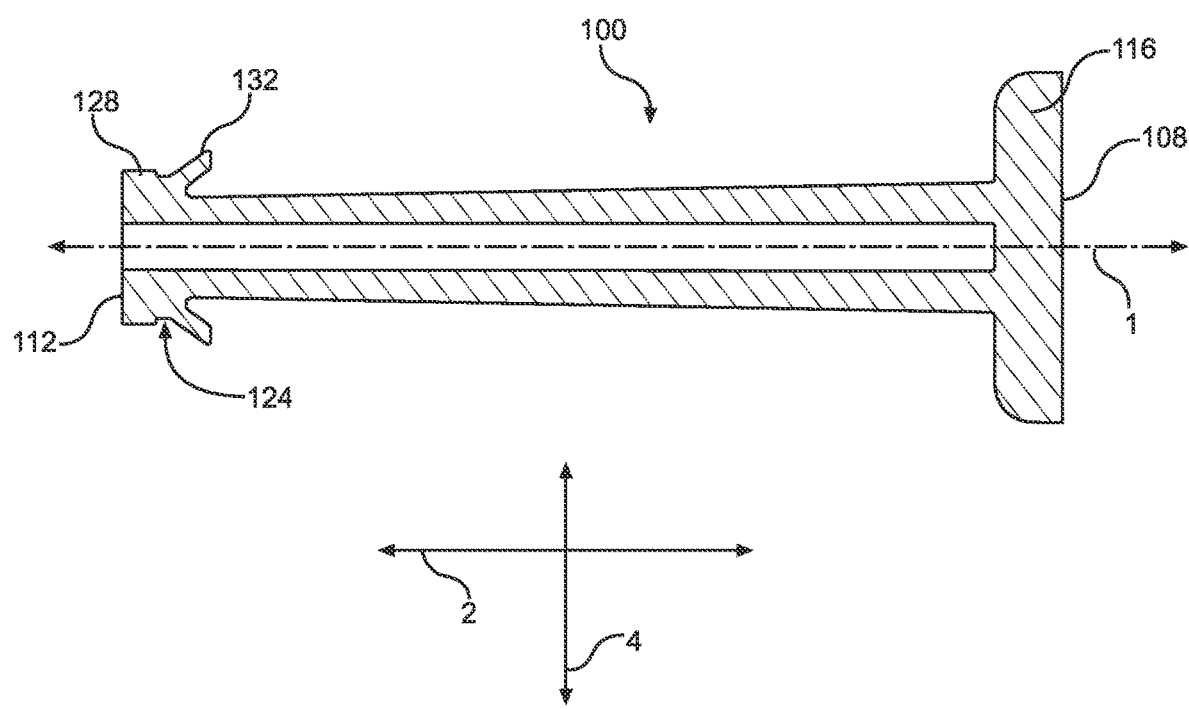
FIG. 7 illustrates a top cross-sectional view of the inner body of FIG. 5.
Figure 8:
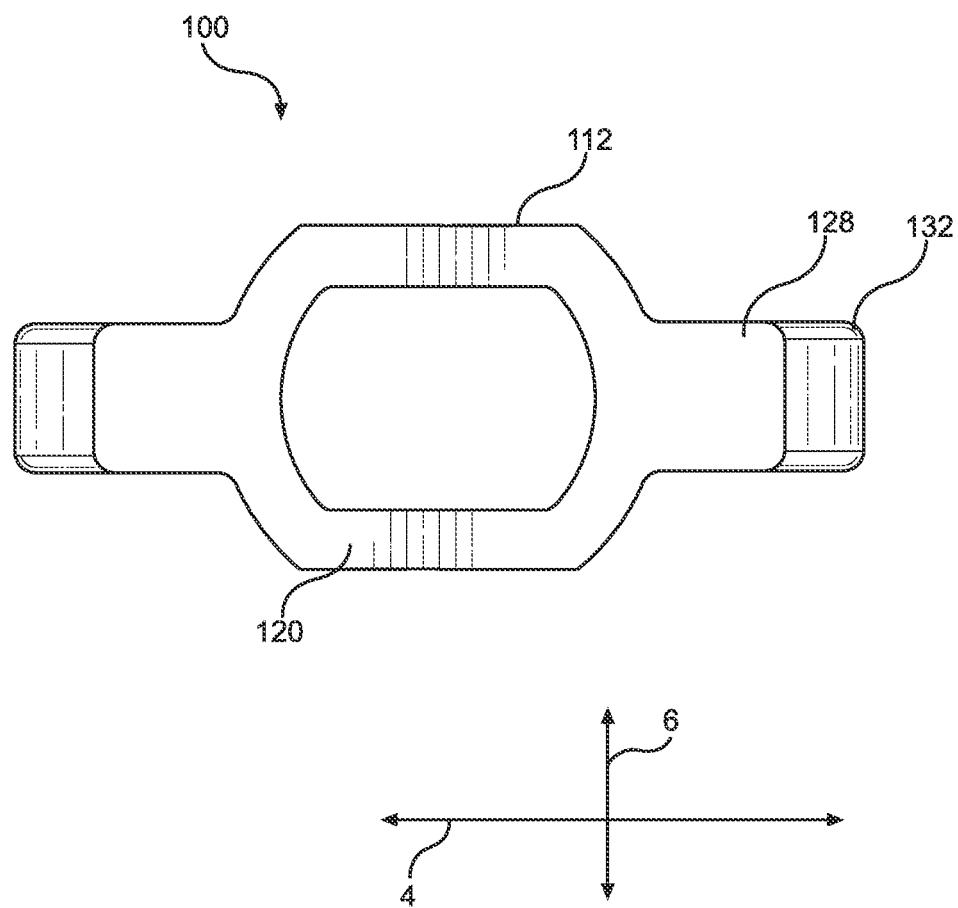
FIG. 8 illustrates a front perspective view of the inner body of FIG. 5.
Figure 9:
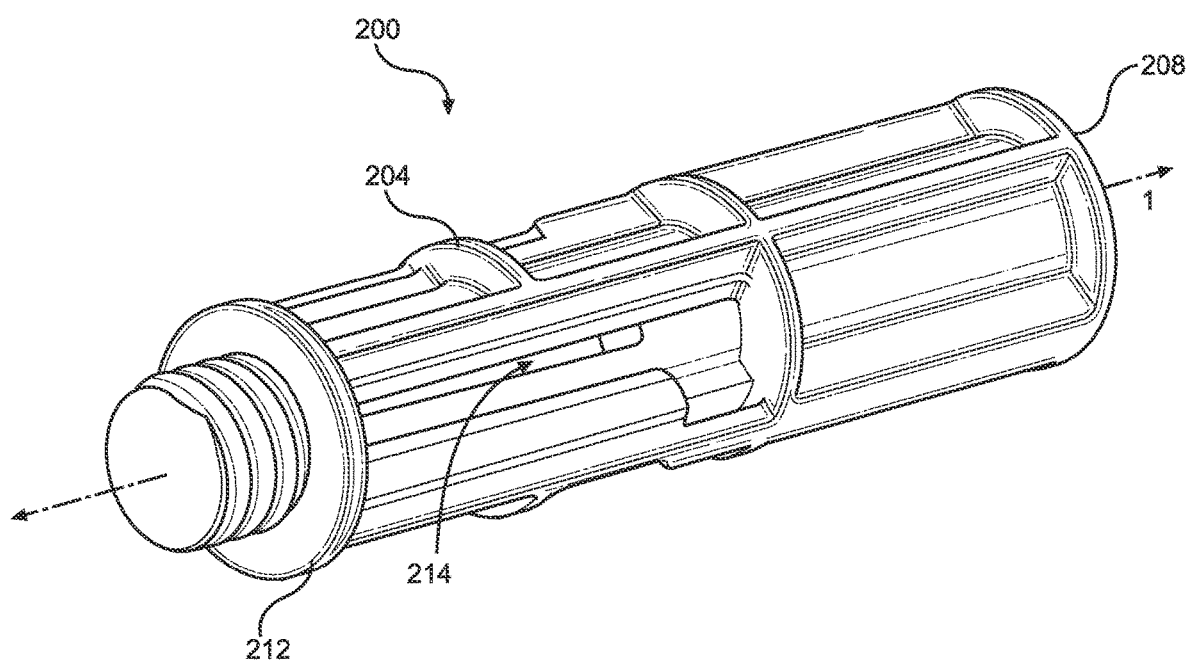
FIG. 9 illustrates an angled perspective view of an outer housing.
Figure 10:
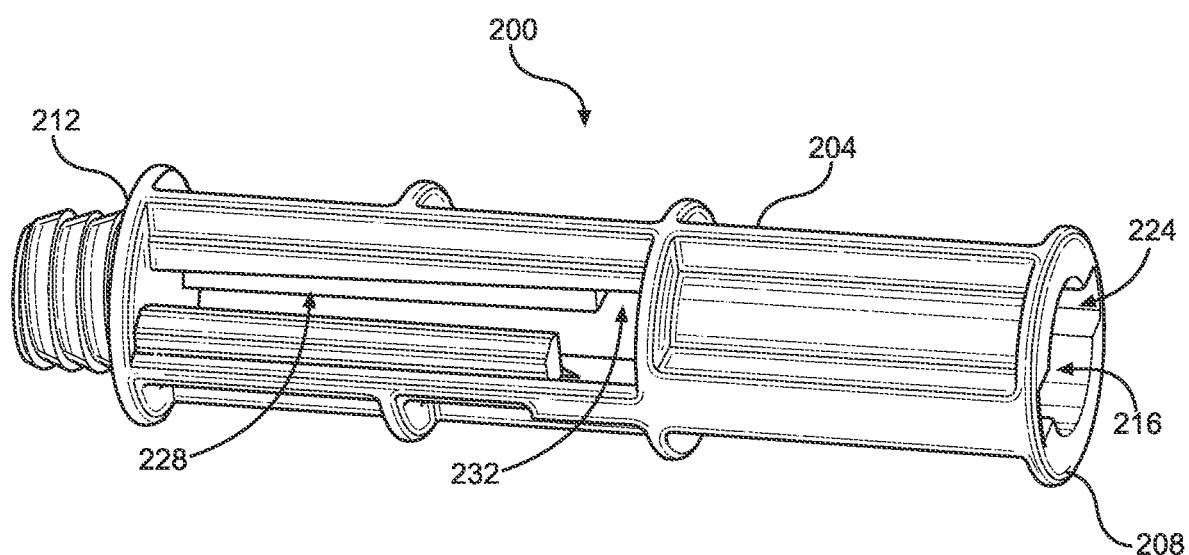
FIG. 10 illustrates another angled perspective view of the outer housing of FIG. 9.

The inner body 100 includes one or more retention members 124 disposed thereon that are configured to selectively engage and disengage with the outer housing 200, as will be described in detail below. In some aspects, such as shown in the figures, the inner body 100 may include two retention members 124 disposed adjacent the distal end 112 of the inner body 100. It will be understood that the quantity of retention members 124 may differ in other embodiments, and the inner body 100 may include 1, 2, 3, . . . 8, or another suitable number of retention members 124 thereon. Further, the position of each retention member 124 may differ in other embodiments, for example, where one or more retention members 124 is/are disposed along the inner body 100 between the proximal end 108 and the distal end 112. As shown in FIG. 5 in detail, each retention member 124 includes a base 128 that is fixedly attached to the inner body 100. The base 128 may extend from the inner body 100 in a direction away from the insertion axis 1, for example, along a transverse direction 4 that is perpendicular to the axial direction 2. A protrusion 132, such as a finger, extends from the base 128. The protrusion 132 is configured to flex or deform upon application of a force thereon as will be described further below. Each retention member 124 may include a single protrusion 132 or, alternatively, a plurality of protrusions 132. This disclosure is not limited to the specific arrangement or quantity of retention members 124 as shown in the figures, and other arrangements are envisioned, such as a plurality of retention members 124 disposed radially around the inner body 100, such that they extend away from the insertion axis 1 in the transverse direction 4, in a lateral direction 6 that is perpendicular to both the transverse direction 4 and the axial direction 2, or in a combination of transverse and lateral directions 4 and 6.

The distal end 112 of the inner body 100 defines a distal face 120. The face 120 has a particular cross-sectional shape when viewed in a plane defined by the transverse and lateral directions 4, 6 (i.e. the plane that is orthogonal to the insertion axis 1). The distal face 120 may be substantially flat such that it lies within a single plane orthogonal to the insertion axis 1. The cross-sectional shape of the face may depend on the shape of the inner body 100 adjacent the distal end 112. In some embodiments, the cross-sectional shape of the face 120 (excluding the base 128) is substantially semicircular. In other embodiments, the cross-sectional shape of the distal face 120 (excluding the base 128) is substantially semicircular except for a step 140 defined thereon. As shown in FIG. 5, for example, the inner body 100 may include a step 140 defined thereon that extends along at least a portion of the inner body 100 between the proximal end 108 and the distal end 112. The dimensions of the step 140 relative to the inner body 100 and the distal end 112 determine the cross-sectional shape of the distal face 120. As shown in FIG. 5, the step 140 may have a length 140A measured along the inner body 100 and extending from the distal end 112. The step 140 further has a width 140B that is measured along a direction perpendicular to the measurement of the length 140A, for example, along the transverse direction 4. The step 140 further includes a depth 140C, which may be measured along a direction perpendicular to the directions of measurement of both the length 140A and the width 140B. The step 140 defines at least a portion of the distal face 120 at the distal end 112 of the inner body 100. The shape and dimensions of the step 140 are selected to profile match a corresponding step on an inner surface of the outer housing 200 in order to minimize the first length 36A when the plunger rod 30 is in the compact configuration while providing for better force distribution from the inner body 100 to the outer housing 200 when the plunger rod 30 is in the extended configuration. The cross-sectional shape and flatness of the distal face 120 can provide advantages in some embodiments of the disclosed syringe assembly 10, as will be discussed further below.

The inner body 100 is configured to movably engage with the outer housing 200. The inner body 100 and the outer housing 200 operate together in a telescoping manner to form the plunger rod 30. The plunger rod 30 is configurable between at least a compact configuration (see, e.g., FIG. 16) and an extended configuration (see, e.g., FIGS. 17 and 18) as will be described in detail below. In the compact configuration, the plunger assembly 30 has a first length (measured between the proximal end 32 and the distal end 34 of the plunger rod 30), and in the extended configuration, the plunger assembly 30 has a second length that is greater than the first length (measured between the proximal end 32 and the distal end 34 of the plunger rod 30). The inner body 100 is disposed within the outer housing 200 in a first position when the plunger rod 30 is in the compact configuration, and in a second position spaced away from the first position along the axial direction 2 when the plunger rod 30 is in the extended configuration. When the inner body 100 is in the first position, the retention members 124 may be received in the respective proximal channels 224, and when the inner body 100 is in the second position, the retention members 124 may be received in the respective distal channels 228.

Referring to FIGS. 9-14, The outer housing 200 includes a housing body 204 that extends between a proximal end 208 and a distal end 212 that is spaced from the proximal end 208 along the axial direction 2. A lumen 214 is defined by the outer housing body 204 and extends between the proximal end 208 and the distal end 212. A proximal opening 216 is defined at the proximal end 208 and is in fluid communication with the lumen 214. The outer housing 200 is configured to receive the inner body 100 into the lumen 214 through the proximal opening 216. In some aspects, the body 204 may have a substantially uniform thickness (measured in a radial direction perpendicular to the axial direction 2 from the insertion axis 1). As such, one or more cutouts may be defined on the body 204 to ensure that the thickness is uniform between the proximal end 208 and the distal end 212. It will be appreciated that the particular thicknesses and uniformity will depend on manufacturing tolerances, materials, preferences, and intended use of the device. In some aspects, the outer housing 200 may include a plunger retention member 42 disposed adjacent the distal end 212 thereon that is configured to receive a plunger 40 thereon, as described above.

The inner body 100 is movable within the lumen 214 between the proximal end 208 and the distal end 212. The lumen 214 is configured to receive the inner body 100 in different orientations along its length between the proximal and distal ends 208, 212. Features defined on or in the body 204 that, at least in part, define the lumen 214 are configured to be contacted by the inner body 100 and to serve as physical guides along which the inner body 100 can move within the lumen 214 and/or as impediments that preclude axial movement of the inner body 100 along the insertion axis 1 in the axial direction 2 and/or rotational movement of the inner body 100 around the insertion axis 1.

Referring again to FIGS. 10-14, the outer housing 200 may include a plurality of channels defined on the body 204 that fluidly communicate with the lumen 214. Each channel can extend along a portion of the length of the outer housing 200 between the proximal end 208 and the distal end 212. Some of the plurality of channels may be spaced relative to each other in the axial direction. In some aspects, one or more channels may overlap with each other along the axial direction 2. The plurality of channels may include a proximal channel 224 and a distal channel 228. The proximal channel 224 may be defined on the body 204 and extend from the proximal end 208 along the axial direction 2 towards the distal end 212 along a predetermined distance. The distal channel 228 may be defined on or in the body 204 and extend from the distal end 212 along the axial direction 2 towards the proximal end 208 along a predetermined distance. The proximal channel 224 may axially overlap with at least a portion of the distal channel 228.

As shown in the figures, the outer housing 200 may include two proximal channels 224 spaced radially around the insertion axis 1 and arranged opposite one another. The proximal channels 224 may have a substantially rectangular cross section when viewed in a plan perpendicular to the axial direction 2. Both of the proximal channels 224 may have the same length and cross-sectional shape. Both of the proximal channels 224 may extend from the proximal end 208 along equal distances. It will be appreciated that the outer housing 200 may include a different number of proximal channels 224, the proximal channels 224 may have a different cross-sectional shape, the proximal channels 224 may be arranged differently relative to one another, and/or each of the proximal channels 224 may differ from at least one of the other proximal channels 224 in one or more characteristics described above.

In some aspects, the outer housing 200 may include two distal channels 228. The distal channels 228 may be arranged radially around the insertion axis 1 and arranged opposite one another. Both distal channels 228 may extend from the distal end 212 along equal distances. The radial arrangement of each of the distal channels 228 around the insertion axis 1 may be angularly offset relative to the radial arrangement of each of the proximal channels 224. The distal channels 228 may be defined partially or entirely through the body 204. In some aspects, the distal channels 228 from the lumen 214 in a radial direction entirely through the body 204.

In some aspects, the proximal opening 216 may be "keyed" such that it defines a particular cross-sectional shape to be configured to receive the inner body 100 only when the inner body 100 is oriented in a complementary orientation. With specific reference to FIGS. 10, 12, and 13, the proximal opening 216 is depicted as being substantially circular (when viewed in a plane orthogonal to the insertion axis 1) and that also defines two proximal channels 224 extending from the proximal opening 216 towards the distal end 212. While two proximal channels 224 are depicted, it will be appreciated that another suitable number of proximal channels 224 may be included. The arrangement of the proximal channels 224 and the proximal opening 216 are configured to complement a cross-sectional shape of the inner body 100. When the inner body 100 is oriented such that its cross-sectional shape corresponds to the cross-sectional shape of the proximal opening 216 and proximal channels 224, the inner body 100 is insertable into the lumen 214 through the proximal opening 216 and the proximal channels 224.

The proximal channels 224 are dimensioned to receive a portion of the inner body 100 therein. In some aspects, the proximal channels 224 are configured to slidably receive the retention members 124. The inner body 100 can slidably move within the outer housing 200, such that the inner body 100 moves within the lumen 214 while the retention members 124, which are affixed to the inner body 100, move within the proximal channels 224. The arrangement of the retention members 124 within the proximal channels 224 can preclude rotation of the inner body 100 around the insertion axis 1 while the retention members 124 are within the respective proximal channels 224. That is, when each retention member 124 is within the respective proximal channel 224, the retention member 124 is configured to contact the outer housing 200 (i.e. the body 204 of the outer housing 200) such that the contact prevents rotation of the retention member 124, and thus prevents rotation of the inner body 100.

The distal channels 228 are similarly dimensioned to receive the retention members 124 therein. As the inner body 100 is moved in the axial direction 2 towards the distal end 212 of the outer housing 200, the retention members 124 may slidably move through and out of the proximal channels 224 in the same axial direction 2. After the retention members 124 have moved out of the proximal channels 224, the retention members 124 may be moved into respective distal channels 228, through which the retention members 124 may be slidably moved in the axial direction 2 as the inner body 100 is also moved through the lumen 214 towards the distal end 212 of the outer housing 200. The distal channels 228 may be dimensioned to preclude rotation of the inner body 100 around the insertion axis 1 while the retention members 124 are within the respective distal channels 228. That is, when each retention member 124 is within the respective proximal channel 228, the retention member 124 is configured to contact the outer housing 200 (i.e. the body 204 of the outer housing 200) such that the contact prevents rotation of the retention member 124, and thus prevents rotation of the inner body 100.

In some aspects, the inner body 100 may need to be rotated around the insertion axis 1 after the retention members 124 have been moved out of the proximal channels 224 but prior to the retention members 124 being moved into the distal channels 228. The outer housing 200 may define an intermediate channel 232 defined on or in the body 204 that is disposed between, or alternatively encompassing portions of, the proximal channels 224 and the distal channels 228. The intermediate channel 232 is configured to receive the inner body 100 and the retention members 124 therein. When in the intermediate channel 232, the inner body 100 and the retention members 124 are configured to be moved along the axial direction 2, either towards the distal end 212 or towards the proximal end 208. In the intermediate channel 232, both the inner body 100 and the retention members 124 thereon are configured to be rotated around the insertion axis 1. That is, rotation of the inner body 100 is not precluded when the retention members 124 are disposed within the intermediate channel 232 unlike when the retention members 124 are disposed in the proximal channels 224 or in the distal channels 228. As the inner body 100 is moved through the proximal channels 224, the inner body 100 may be rotated around the insertion axis 1 when the retention members 124 are disposed in the intermediate channel 232 prior to being further moved into and through the distal channels 228.

Figure 14:
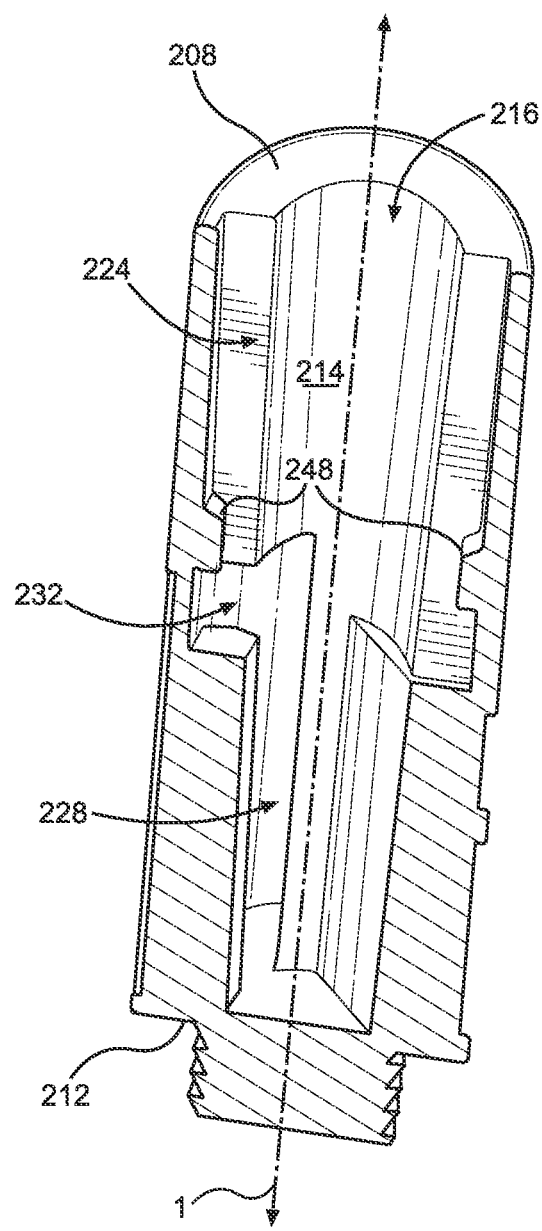
FIG. 14 illustrates another side cross-sectional view of the outer housing of FIG. 9.

Upon assembly of the plunger rod 30, the inner body 100 is introduced into the outer housing 200 as described above. In some scenarios, it may be preferable to preclude easy separation of the inner body 100 from the outer housing 200 after assembly. To this end, in some aspects, the outer housing 200 and/or the inner body 100 may include one or more features that are configured to allow connection of the outer housing 200 with the inner body 100 but impede separation of the outer housing 200 from the inner body 100. Referring to FIG. 14, the housing body 204 may define a plurality of detents 248 extending into the lumen 214. In particular embodiments, the detents 248 may extend into the proximal channels 224. As shown in the exemplary embodiments of the figures, each of the two proximal channels 224 may include a detent 248. However, it will be appreciated that the detents 248 may be disposed along other portions of the lumen 214. It should be further understood that, although two detents 248 are depicted, the outer housing 200 may include a different number of detents, such as 1, 2, 3, . . . 8, or more detents 248. Although each of the two proximal channels 224 includes a detent 248, other aspects may be designed such that some of the proximal channels 224 include a detent 248 while others do not.

In operation, the inner body 100 may be slidably moved along the axial direction 2 towards the distal end 212 of the outer housing 200 until the inner body 100 contacts the detents 248. The inner body 100 and the detents 248 may be configured such that the inner body 100 is permitted to slidably move past the detents 248 towards the distal end 212, but be precluded from moving backwards past the detents 248 towards the proximal end 208. In some aspects, the retention members 124 of the inner body 100 may be configured to physically interact with the detents 248. As shown in FIGS. 5-8 and described above, each retention member 124 may include a base 128 and a protrusion 132. The protrusion 132 may be deformable, for example, in a radial direction towards the insertion axis 1. As the inner body 100 is moved through the proximal channels 224, the retention members 124 may contact the respective detents 248 disposed within the proximal channels 224. In some aspects, each protrusion 132 may contact each respective detent 248. As the inner body 100 is moved towards the distal end 212 of the outer housing 200, each protrusion 132 can deflect and slide over the respective detent 248. The protrusion 132 may be resilient. When the inner body 100 is further moved towards the distal end 212 and the protrusion 132 moves past the detent 248, the protrusion 132 can revert to substantially its original, un-deformed position before it was deflected. The protrusions 132 and the detents 248 are configured to allow the protrusions 132 to flex and slide over the detents 248 when the inner body 100 is moved towards the distal end 212, but to prevent the protrusions 132 from flexing and sliding over the detents 248 when the inner body 100 is moved towards the proximal end 208. That is, after the protrusions 132 have passed over the detents 248 and moved back to their un-deformed positions, if the inner body 100 is moved towards the proximal end 208, the retention members 124 contact the detents 248 and do not slide over the detents. Thus, the detents 248 serve as physical barriers that preclude removal of the inner body 100 from the outer housing 200 (see FIG. 22, for example). It will be appreciated that sufficient force should be applied to the inner body 100 towards the distal end 212 of the outer housing 200 such that the applied force is enough to overcome the material resistance of the flexible protrusions 132 to cause the protrusions 132 to deflect and slide over the detents 248.

It should be understood that in other aspects, the arrangement described above can be reversed, such that the detents 248 are disposed on the inner body 100 while the retention members 124 having flexible protrusions 132 are disposed on the outer housing 200.

Figure 15A:
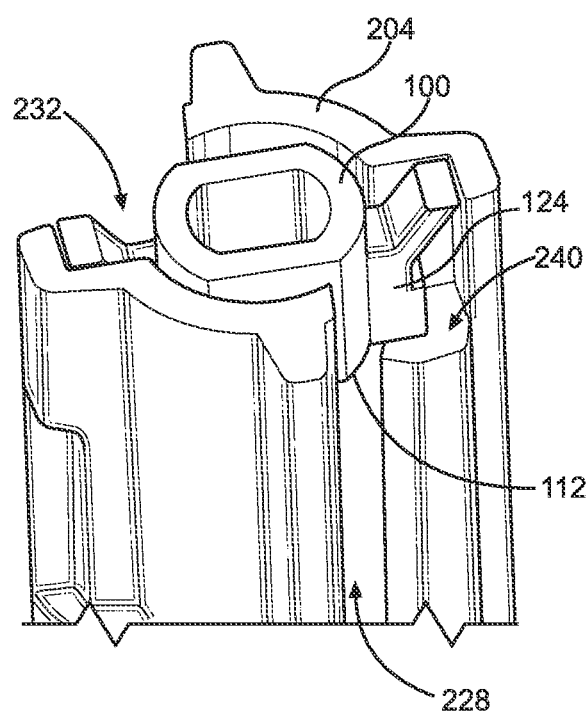
FIG. 15A illustrates a cross-sectional view of a plunger rod with the inner body in a first rotational position relative to the outer housing.
Figure 15B:
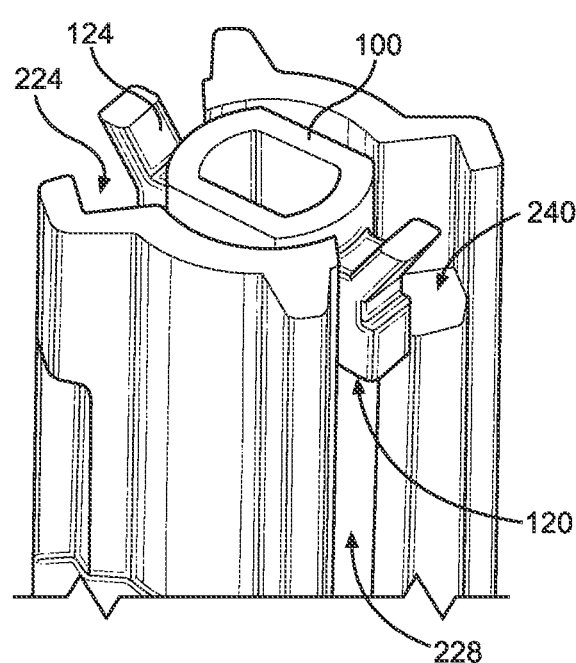
FIG. 15B illustrates a cross-sectional view of the plunger rod of FIG. 15A but with the inner body in a second rotational position relative to the outer housing.

After the inner body 100 has been moved through the lumen 214 such that the retention members 124 are entirely within the intermediate channel 232 (i.e. when the retention members 124 and the proximal channels 224 do not together obstruct rotation of the inner body 100), the inner body 100 can be rotated around the insertion axis 1 such that the retention members 124 are in alignment with the distal channels 228. Once aligned, the inner body 100 can be moved further towards the distal end 212 of the outer housing 200 through the distal channels 228. Referring to FIGS. 15A and 15B, two different rotational alignments are depicted. FIG. 15A shows a cross-sectional view of an inner body 100 being aligned relative to the outer housing 200 such that the retention members 124, while being disposed in the intermediate channel 232, are aligned with the proximal channels 224 to be axially movable within the proximal channels 224. FIG. 15B shows the inner body 100 being in a different rotational position relative to FIG. 15A, where the inner body 100 in FIG. 15B is aligned relative to the outer housing 200 such that the retention members 124 in the intermediate channel 232 are aligned with the distal channels 228 so as to be axially movable within the distal channels 228. When the retention members 124 are aligned with the proximal channels 224, the retention members 124 are not configured to move within the distal channels 228; conversely, when the retention members 124 are aligned with the distal channels 228, the retention members 124 are not configured to move within the proximal channels 224.

Figure 11:
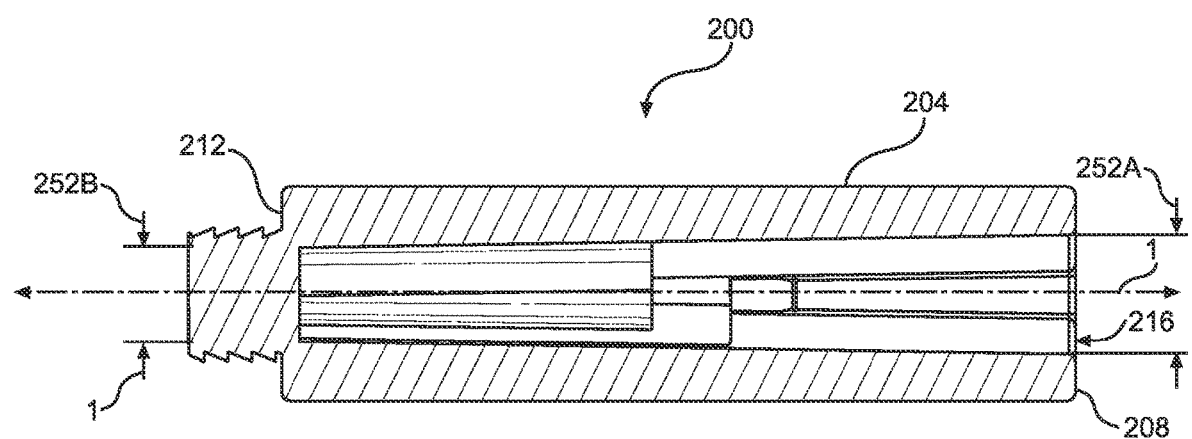
FIG. 11 illustrates a side cross-sectional view of the outer housing of FIG. 9.
Figure 12:
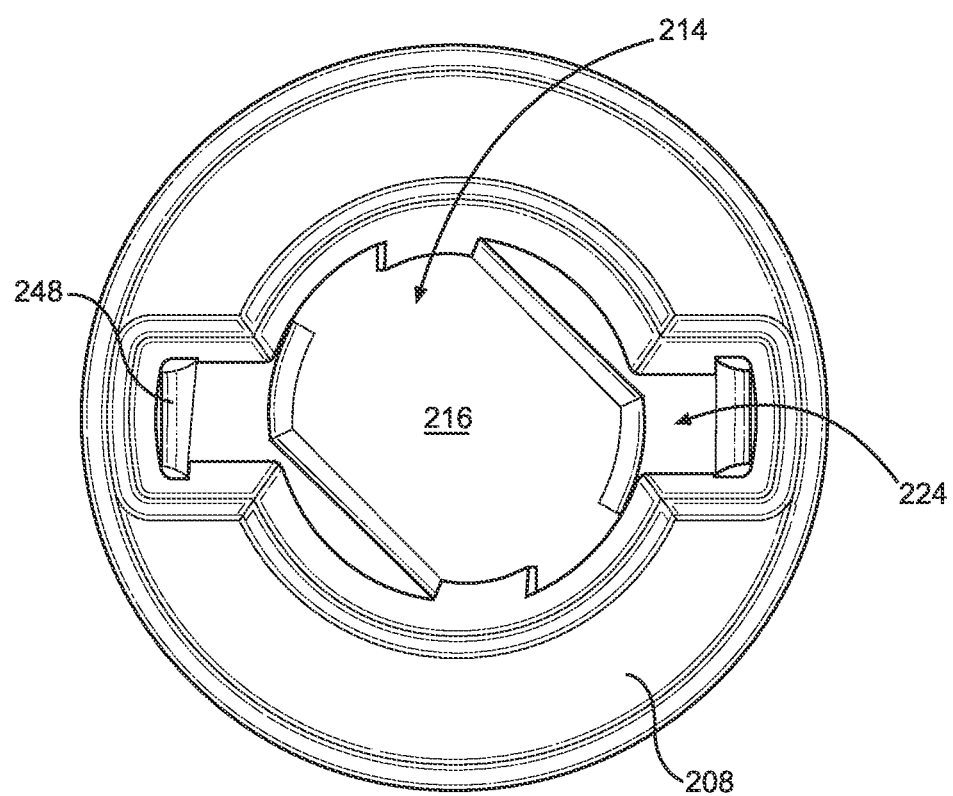
FIG. 12 illustrates a back perspective view of the outer housing of FIG. 9.

In some aspects, the lumen 214 of the outer housing 200 may be tapered from the proximal end 208 towards the distal end 212. As shown in FIG. 11, the lumen 214 may include a first cross-sectional diameter 252A and a second cross-sectional diameter 252B spaced from the first cross-sectional diameter 252A along the axial direction 2. The first cross-sectional diameter 252A may be closer to the proximal end 208 than is the second cross-sectional diameter 252B. In some aspects, the first cross-sectional diameter 252A may be adjacent the proximal end 208, and the second cross-sectional diameter 252B may be adjacent the distal end 212. In some aspects, the second cross-sectional diameter 252B may be smaller than the first cross-sectional diameter 252A. The second cross-sectional diameter 252B of the lumen 214 may be dimensioned to be slightly larger than the second cross-sectional dimension 136B of the inner body 100 such that, as the inner body 100 is moved towards the distal end 212 of the outer housing 200, the inner body 100 is configured to contact the body 204 of the outer housing 200 adjacent the second cross-sectional diameter 252B of the lumen 214. That is, a friction fit can be formed between the inner body 100 and the outer housing 200 adjacent the distal end 212 of the outer housing 200. A friction fit between the inner body 100 and the body 204 of the outer housing 200 when the inner body 100 is fully inserted into the outer housing 200 (i.e. when the inner body 100 is moved to its farthest possible position along the axial direction 2 towards the distal end 212 of the housing) allows for the inner body 100 to be secured relative to the outer housing 200 until a sufficient force is applied to the inner body 100 and/or the outer housing 200 to overcome the friction between the inner body 100 and the outer housing 200 and cause the inner body 100 to axially move relative to the outer housing 200 towards the proximal end 208.

Figure 13:
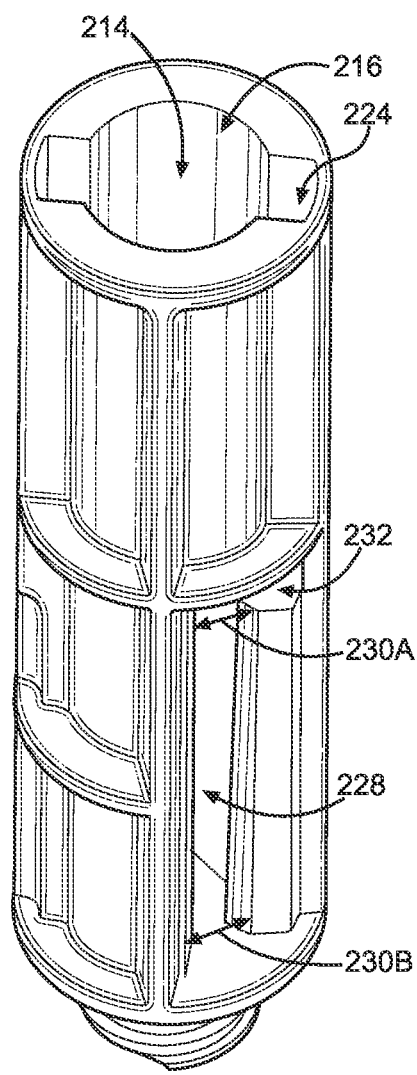
FIG. 13 illustrates another angled perspective view of the outer housing of FIG. 9.

In some aspects, the distal channels 228 may be tapered along their respective lengths as they extend from the intermediate channel 232 towards the distal end 212 of the outer housing 200. As the inner body 100 is slidably moved along the lumen 214 towards the distal end 212 and the retention members 124 slidably move within the distal channels 228, a friction fit may be formed between the retention members 124 and the body 204 that defines the distal channels 228 adjacent the distal end 212. This friction fit can be caused by the tapering of the distal channels 228. It will be understood that the distal channels 228 should be sized such that the retention members 124 can slidably pass therein at least until the inner body 100 reaches its distal-most position and is precluded from further movement towards the distal end 212 along the axial direction 2. The friction fit between the body 204 and the retention members 124 when the retention members are in the distal channels 228 can help secure the inner body 100 relative to the outer housing 200 until a sufficient force is applied to the inner body 100 and/or the outer housing 200 to overcome the friction fit between the retention members 124 and the housing body 204 that defines the distal channels 228 to cause the inner body 100 to axially move relative to the outer housing 200 towards the proximal end 208. Referring to FIG. 13, each distal channel 228 may have a first width 230A and a second width 230B spaced from the first width 230A towards the distal end 212 along the axial direction 2. The first and second widths 230A and 230B can be measured between the portions of the body 204 that define the distal channel 228, for example along a direction perpendicular to the axial direction 2. The second width 230B may be smaller than the first width 230A. Both the first and second widths 230A, 230B should be sized such that a retention member 124 of the inner body 100 is configured to pass into the distal channel 228 defined by the body 204. In some aspects, the second width 230B may be only slightly larger than the retention member 124, such that the distal channel 228 at the second width 230B is configured to receive the retention member 124 therein at the second width 230B such that the retention member 124 is in contact with both sides of the body 204 that defines the distal channel 228. In some aspects, the first width 230A may be adjacent to the intermediate channel 232. The second width 230B may be adjacent to the distal end 212 of the outer housing 200.

Figure 16:
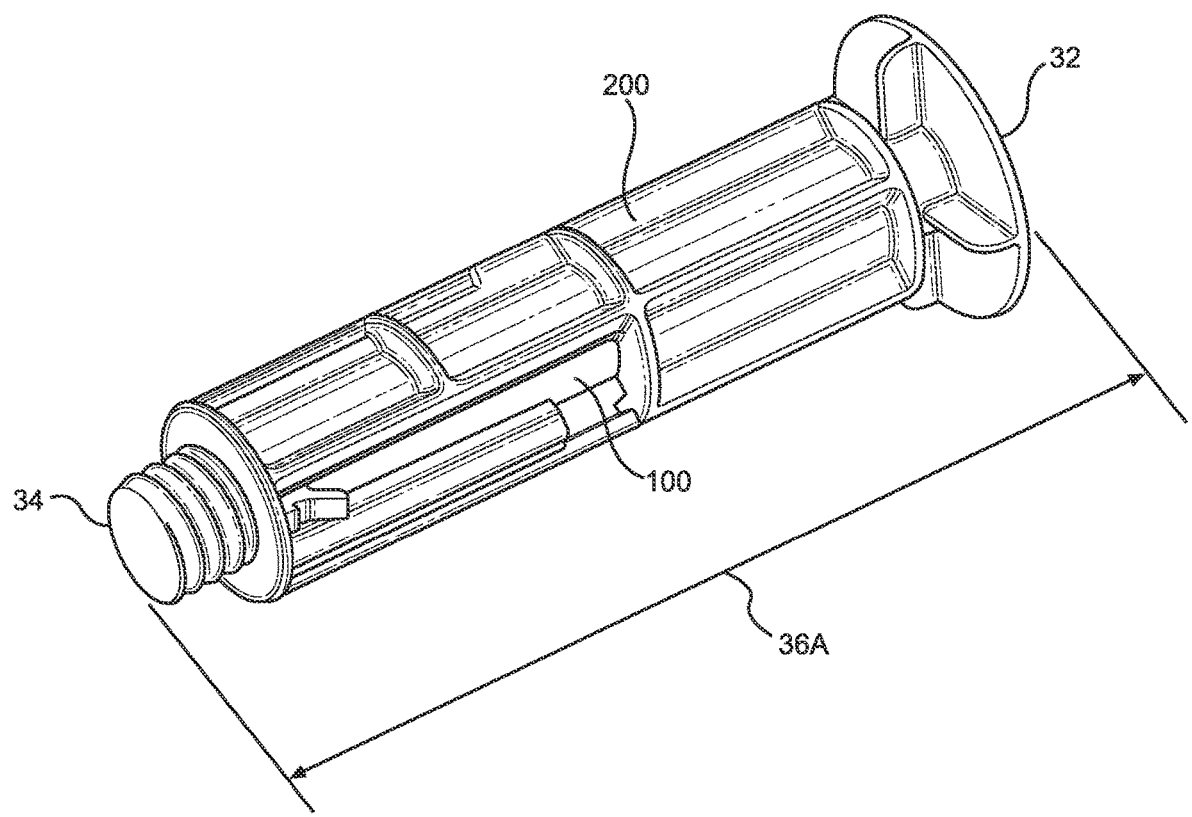
FIG. 16 illustrates an angled perspective view of a plunger rod being in the compact configuration.
Figure 17:
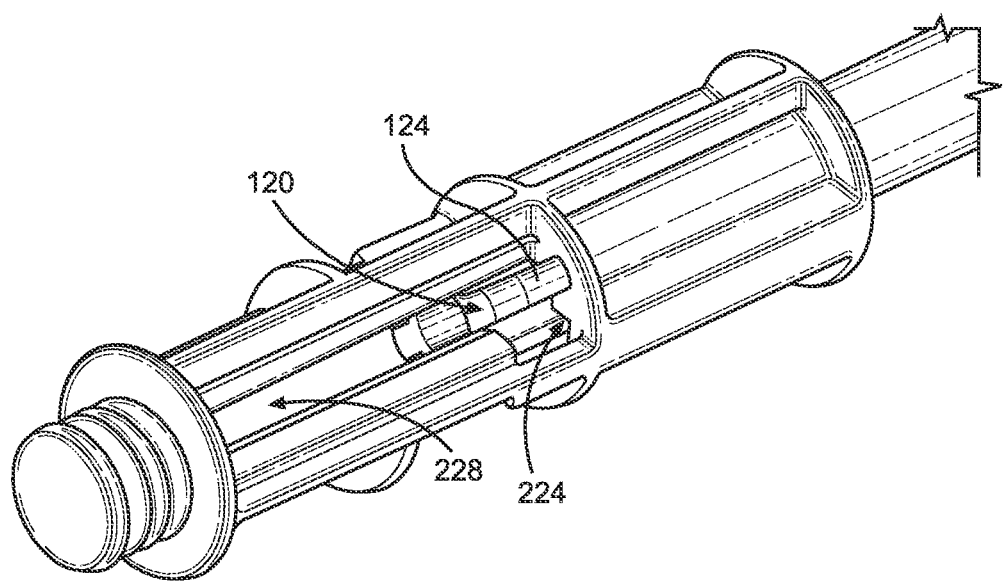
FIG. 17 illustrates an angled perspective view of the plunger rod of FIG. 16 in an extended, unlocked configuration.
Figure 18:
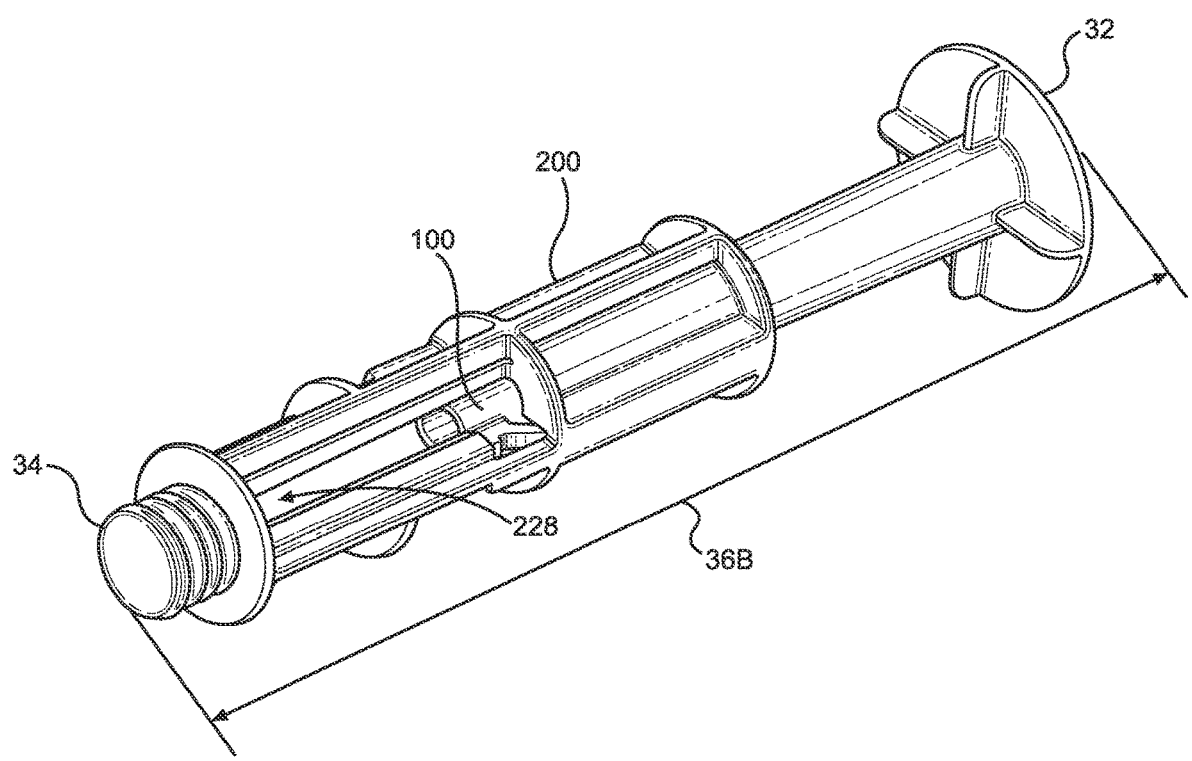
FIG. 18 illustrates an angled perspective view of the plunger rod of FIG. 16 in an extended, locked configuration.
Figure 19:
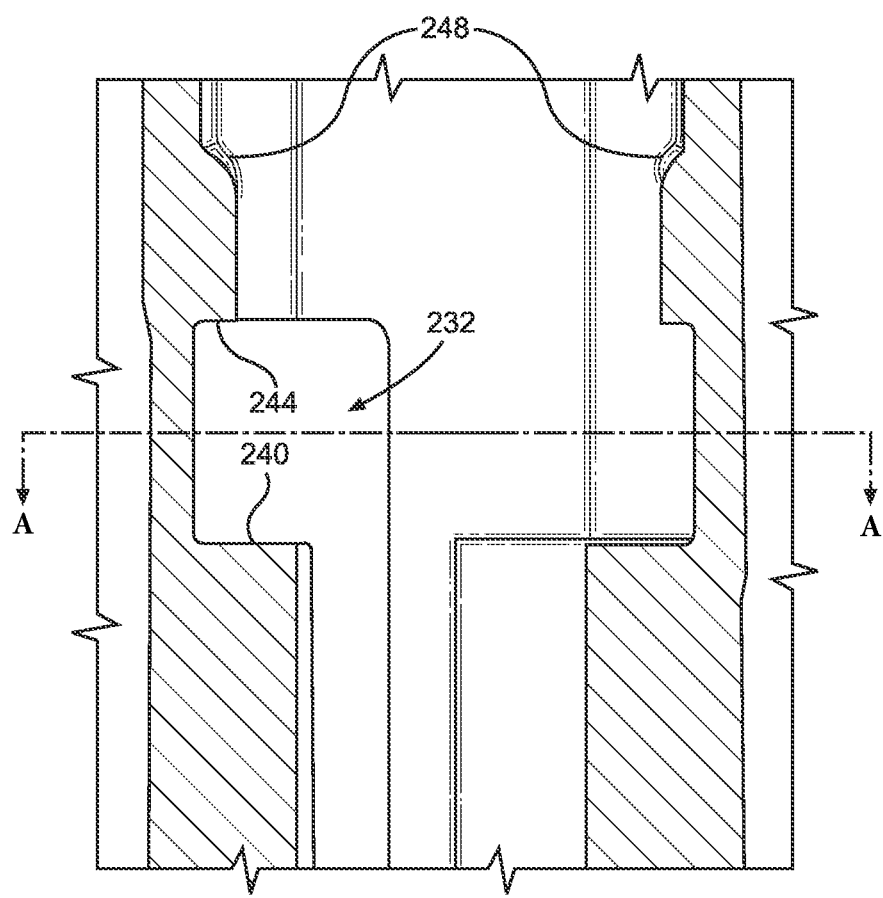
FIG. 19 illustrates a side cross-sectional view of a portion of an outer housing.

In some aspects, for example as shown in FIG. 16, the inner body 100 and the outer housing 200 may be assembled together, such that the inner body 100 is disposed within the distal channels 228 and the inner body 100 is disposed at its distal-most position relative to the outer housing 200, such that the distal end 112 of the inner body 100 is adjacent the distal end 212 of the outer housing 200. In this position, which can be referred to as the "compact" position, the plunger assembly 30 has a first length 36A measured between the proximal end 32 and the distal end 34 along the axial direction 2. The inner body 100 can be slidably moved along the axial direction 2 towards the proximal end 208 of the outer housing 200 until the inner body 100 is disposed at its proximal-most position within the outer housing 200 (for example, when the inner body 100 is moved towards the proximal end 208 until the retention members 124 are placed in contact with the detents 248). Referring to FIGS. 17 and 18, at this position, which can be referred to as the "extended" position, the plunger assembly 30 has a second length 36B measured between the proximal end 32 and the distal end 34 along the axial direction 2. The second length 36B is greater than the first length 36A.

The plunger rod 30 may be operationally connected with a pre-filled syringe 12 and arranged in the compact configuration. In operation, a user can expand the plunger rod 30 from the compact configuration to the extended configuration. When the plunger rod 30 is in the extended configuration (i.e. when the inner body 100 is in the second position) and also in the locked configuration, the user can apply a force onto the inner body 100 (for example at the handle 116) to cause the inner body 100 and the outer housing 200 to move axially within the chamber 14 of the syringe 12, in turn causing liquid material inside the chamber 14 to be dispensed through the distal opening 22 at the distal end 18 of the syringe barrel 13. The force applied to the inner body 100 can be transferred to the outer housing 200 via the contact between the distal face 120 of the inner body 100 and the lower contact surface 240 of the outer housing 200 when the plunger rod 30 is in the locked configuration. Packaging the plunger rod 30 in the compact configuration provides for a smaller physical footprint and allows for less packing material to be used. For example, the length of the syringe assembly 10, measured between the proximal end 11 and the distal end 15, is smaller when the plunger rod 30 is in the compact configuration than when the plunger rod 30 is in the extended configuration. A smaller footprint also allows for physically smaller packages that include all components that would otherwise take up more space, increasing required storage and transportation space, as well as making the packages longer and more unwieldy. The compact footprint makes it easier for a user to remove the syringe assembly 10 from the packaging and prepare it for use. The compact arrangement allows for multiple benefits simultaneously, including, but not limited to, having a smaller packed footprint of all components while simultaneously allowing for the plunger rod 30 to be affixed with the syringe 12, which allows for the syringe 12 to be pre-filled with the desired material prior to arrival to the user.

When the syringe assembly 10 is removed from the packaging, the user may need to transition the plunger rod 30 from the compact configuration to the extended configuration prior to using the syringe assembly 10. The inner body 100 is in its distal-most position relative to the outer housing 200 when the plunger rod 30 is in the compact configuration (see FIG. 16) and in its proximal-most position relative to the outer housing 200 when the plunger assembly is in the extended configuration (see FIGS. 17 and 18). The transitioning process may include the step of moving one of the inner body 100 and the outer housing 200 relative to the other of the inner body 100 and the outer housing 200 along the axial direction 2, such that the inner body 100 is disposed in its proximal-most position relative to the outer housing 200. The movement of the inner body 100 from its distal-most position can include moving the retention members 124 through the distal channels 228 of the outer housing 200 (or, alternatively, moving the outer housing 200 such that the distal channels 228 move relative to the retention members 124). When the inner body 100 is in its distal-most position in the extended configuration, the retention members 124 may be disposed in the intermediate channel 232.

The process may also include the step of securing the inner body 100 relative to the outer housing 200 such that relative movement between the inner body 100 and the outer housing 200 in the axial direction 2 is precluded. The inner body 100 may be rotated around the insertion axis 1 relative to the outer housing 200 such that the retention members 124 are moved out of alignment with the distal channels 228. At this position, the inner body 100 cannot be moved through the distal channels 228 in the axial direction 2 towards the distal end 212. As such, when a force is applied to the inner body 100, the force is translated along the inner body 100 to the body 204 of the outer housing 200, which in turn can slidably move within the syringe 12 to cause dispensing of the material therein. The relative rotation between the inner body 100 and the outer housing 200 may be any suitable angle, such as between about 10 degrees and about 90 degrees, between about 30 degrees and about 60 degrees, or another suitable angle. In some aspects, the inner body 100 may be rotated relative to the outer housing 200 (or vice versa) by approximately 45 degrees.

Referring to FIG. 16, the plunger rod 30 is in the compact configuration, where the inner body 100 is in its distal-most position inside the lumen 214 of the outer housing 200. The retention members 124 of the inner body 100 are disposed within the distal channels 228, and the distal end 112 of the inner body 100 is adjacent the distal end 212 of the outer housing 200. Referring to FIGS. 17 and 18, the plunger rod 30 is in the extended configuration, where the inner body 100 is in its proximal-most position inside the lumen 214 of the outer housing 200 between the distal end 212 and the detents 248. It will be appreciated that, as described above, the detents 248 may preclude proximal movement of the inner body 100 along the axial direction 2 away from the distal end 212 when the retention members 124 contact the detents 248, and, accordingly, for purposes of this description, in aspects depicted having the engagement between the retention members 124 and the detents 248, the proximal-most position of the inner body 100 is the position of the inner body 100 within the lumen 214 when the retention members 124 are between the distal end 212 and the detents 248 and are in contact with the detents 248. Referring specifically to FIG. 17, the inner body 100 is in its proximal-most position, and the retention members 124 are in alignment with the distal channels 228. That is, the inner body 100 can be moved towards the distal end 212 along the axial direction 2. This can be referred to as the "unlocked" configuration. Referring now to FIG. 18, the inner body 100 in its proximal-most position is now shown having been rotated along the insertion axis 1 relative to the outer housing 200. In this position, the retention members 124 are no longer in alignment with the distal channels 228. This can be referred to as the "locked" configuration. At this position, the user can apply a force to the inner body 100 to cause movement of the outer housing 200 through the syringe 12.

Figure 20:
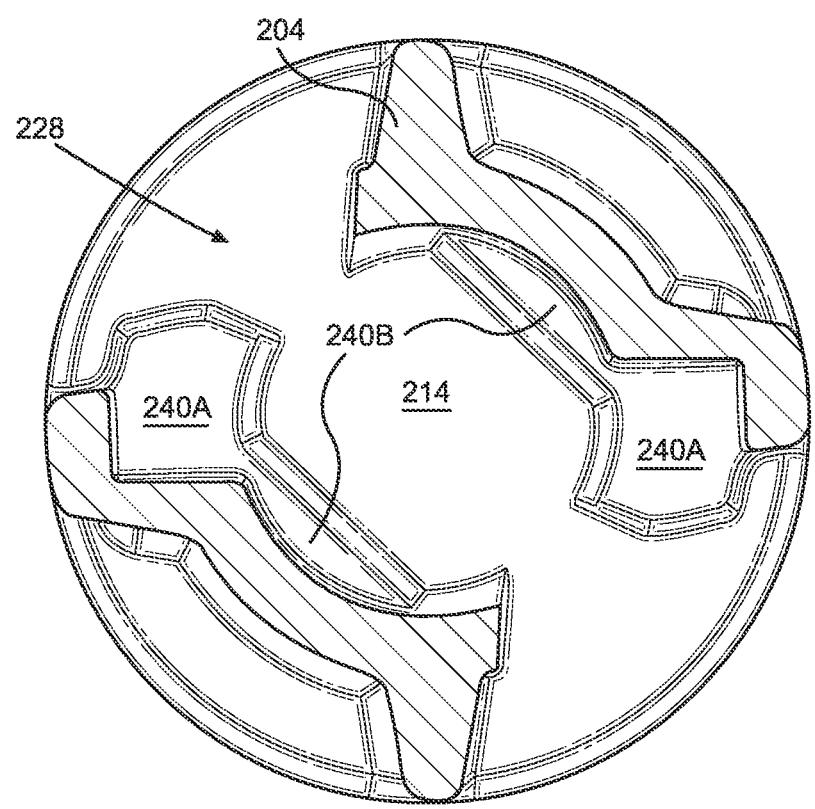
FIG. 20 illustrates a cross-sectional view of the outer housing of FIG. 19 along the line A-A.
Figure 21A:
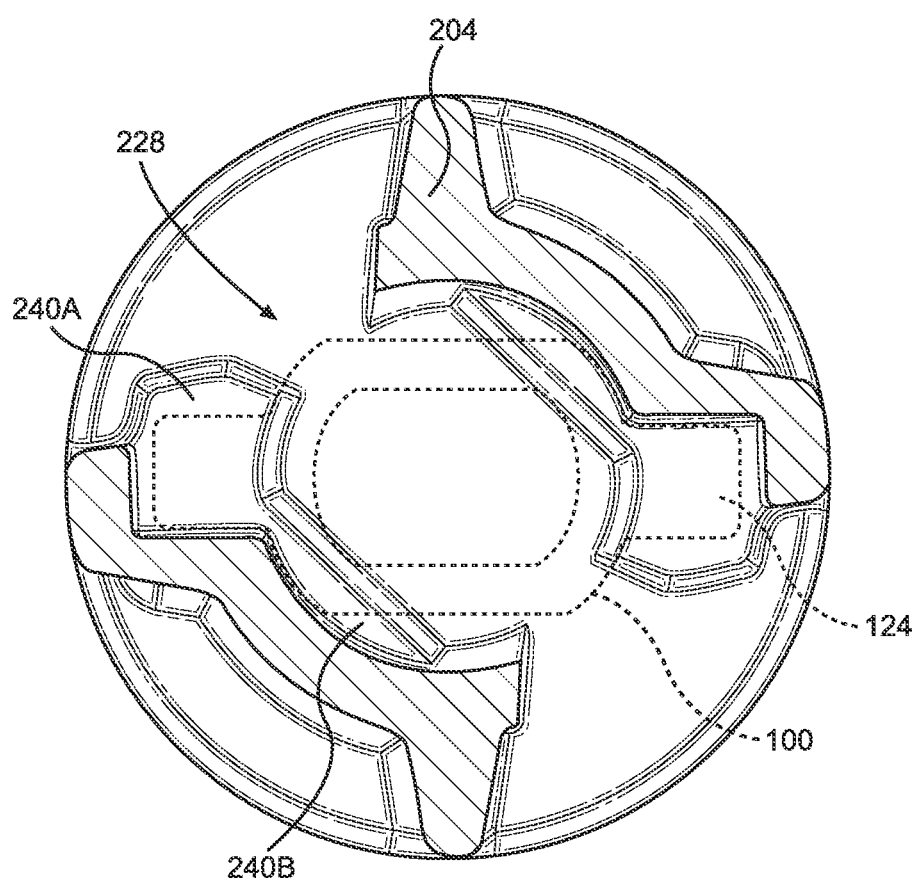
FIG. 21A illustrates a cross-sectional view of a plunger rod showing the inner body in a locked configuration.

When the plunger rod 30 is in the locked configuration, the distal face 120 of the inner body 100 is configured to contact a portion of the body 204 of the outer housing 200. Referring to FIGS. 19-22 (and also referring back to FIGS. 15A and 15B), in some aspects, the outer housing 200 may define a lower contact surface 240 that defines, in part, the intermediate channel 232. The lower contact surface 240 may communicate with the lumen 214. The lower contact surface 240 may be substantially planar defined by the transverse and lateral directions 4 and 6 and orthogonal to the axial direction 2. The lower contact surface 240 may be configured to be placed into contact with the distal face 120 of the inner body 100. When the inner body 100 is in the second position, the inner body 100 may be rotated relative to the outer housing 200 such that the distal face 120, at least partly, axially aligns with the lower contact surface 240. In this position, the distal face 120 is configured to contact the lower contact surface 240. As shown in FIG. 20, the lower contact surface 240 may include at least two different portions, depicted as 240A and 240B. Each portion of the lower contact surface 240 may be configured to contact a portion of the inner body 100. In some aspects, 240A may correspond to a retention member lower contact surface 240A, and 240B may correspond to an inner body lower contact surface 240B. The retention member lower contact surface 240A is configured to be contacted by at least one of the retention members 124 disposed on the inner body 100. The inner body lower contact surface 240B is configured to be contacted by a portion of the step 140 of the inner body 100, for example by the distal end 112 of the inner body 100. Referring to FIG. 21A, the distal end 112 of the inner body 100 is shown transparently to indicate where the distal face 120 of the inner body 100 can contact the lower contact surface 240 of the outer housing 200. As shown in FIG. 21A, the portion of the distal face 120 defined by the retention members 124 is configured to contact the retention member lower contact surfaces 240A. The portion of the distal face 120 defined by the inner body 100 that does not include the retention members 124 is configured to contact the inner body lower contact surface 240B. Contacting the lower contact surface 240 with both the retention members 124 and the inner body 100 allows for better force distribution from the inner body 100 to the outer housing 200 (e.g. when a force is applied by the user to the inner body 100 towards the outer housing 200). Contacting the lower contact surface 240 at the inner body lower contact surface 240B with the inner body 100 also increases durability of the connection and helps spread the force across a larger surface area of the distal face 120 than if the distal face 120 only contacted the lower contact surface 240 between the retention members 124 and the retention member lower contact surface 240A. The presence of the inner body lower contact surfaces 240B additionally provides physical barriers that define the intermediate channel 232 and the distal channels 228, thus acting as physical guides for the inner body 100 when the inner body 100 is aligned with, and being moved through, the distal channels 228. In some aspects, the distal face 120 may be planar and defined by the transverse and lateral directions 4 and 6 such that the distal face 120 is parallel to the lower contact surface 240.

Figure 21B:
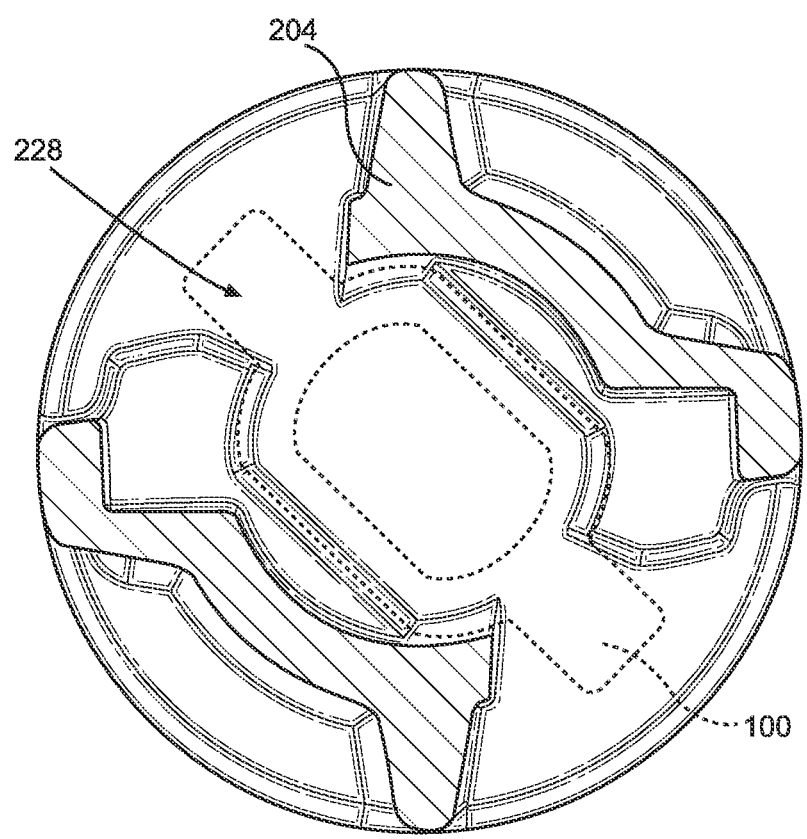
FIG. 21B illustrates a cross-sectional view of the plunger rod of FIG. 21A in an unlocked configuration.

When the inner body 100 is rotated around the insertion axis 1 such that the retention members 124 are aligned with the distal channels 228 as described above, the distal face 120 is no longer in contact with and is no longer in axial alignment with along the axial direction 2 with the lower contact surfaces 240. Referring to FIG. 21B, the distal end 112 of the inner body 100 is shown transparently in the rotated orientation such that the inner body 100 is configured to be slidably received into the distal channels 228, where the distal face 120 is out of alignment with the lower contact surfaces 240.

Figure 22:
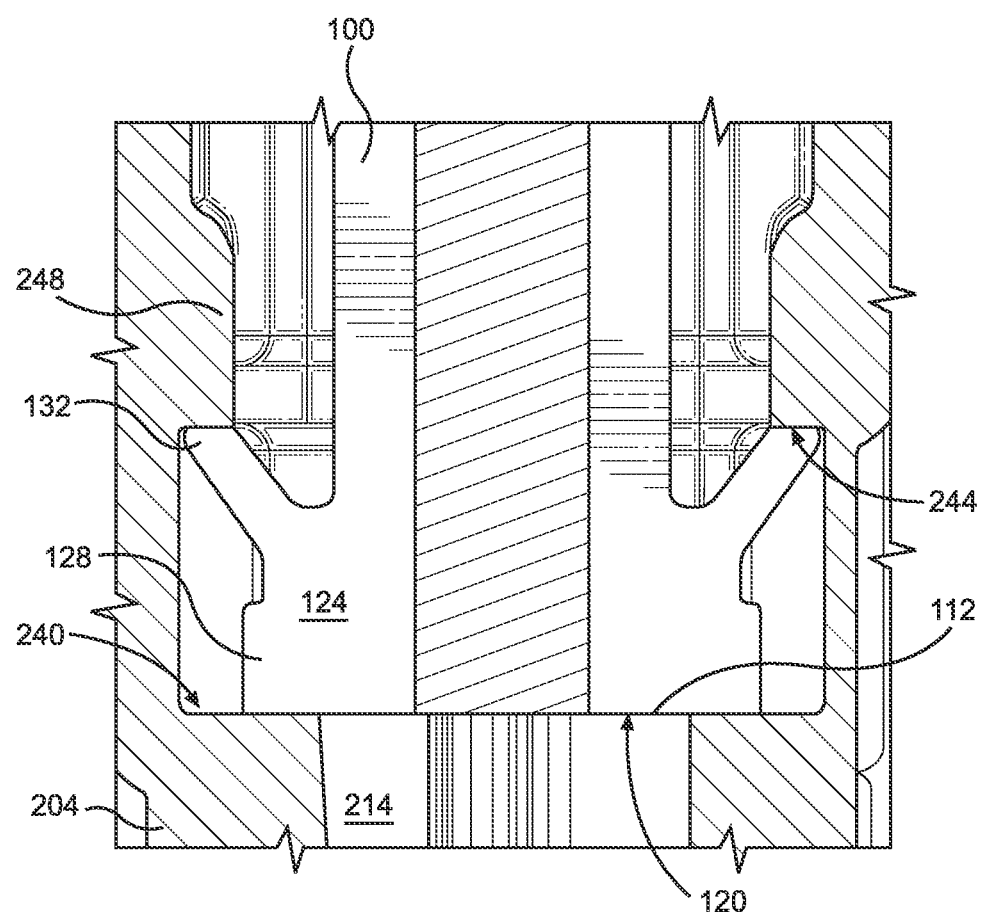
FIG. 22 illustrates a cross-sectional view of the plunger rod of FIG. 21A.

The intermediate channel 232 is further defined by an upper contact surface 244 defined on the housing body 204 and spaced from the lower contact surface 240 along the axial direction 2 toward the proximal end 208 of the outer housing 200. When the plunger rod 30 is in the locked configuration, at least a portion of the inner body 100 can be disposed in the intermediate channel 232 in a space defined between the lower contact surface 240 and the upper contact surface 244. Referring to FIG. 22, the retention members 124 may be disposed between the lower and upper contact surfaces 240, 244. In some aspects, the distance between the lower and upper contact surfaces 240, 244 may be only slightly greater than the length of the inner body 100 that includes the retention members 124 along the axial direction 2 such that the intermediate channel 232 between the lower and upper contact surfaces 240, 244 is configured to receive the retention members 124 therein when the inner body 100 is rotated around the insertion axis 1 but to preclude movement of the retention members 124 along the axial direction 2. In such aspects, the retention members 124 may be configured to contact both the lower contact surface 240 and the upper contact surface 244. The base 128 of each retention member 124 (which can define, in part, the distal face 120) may be configured to contact the lower contact surface 240, and the protrusion 132 may be configured to contact the upper contact surface 244. Each retention member 124 may be in friction fit with the lower and upper contact surfaces 240, 244 when the retention member 124 is received between the lower and upper contact surfaces 240, 244 when the plunger assembly is moved from the unlocked configuration to the locked configuration. Such friction fit may resist relative rotation between the inner body 100 and the outer housing 200 to move the distal face 120 out of contact with the lower contact surface 240 and/or the upper contact surface 244. Such a friction fit can help prevent inadvertent transition of the plunger rod 30 from the locked configuration to the unlocked configuration. To move the plunger rod 30 from the locked to the unlocked configuration, a predetermined rotational force can be applied to the inner body 100 that is sufficient to overcome the frictional connection between the retention members 124 and the lower and upper contact surfaces 240, 244.

Figure 23A:
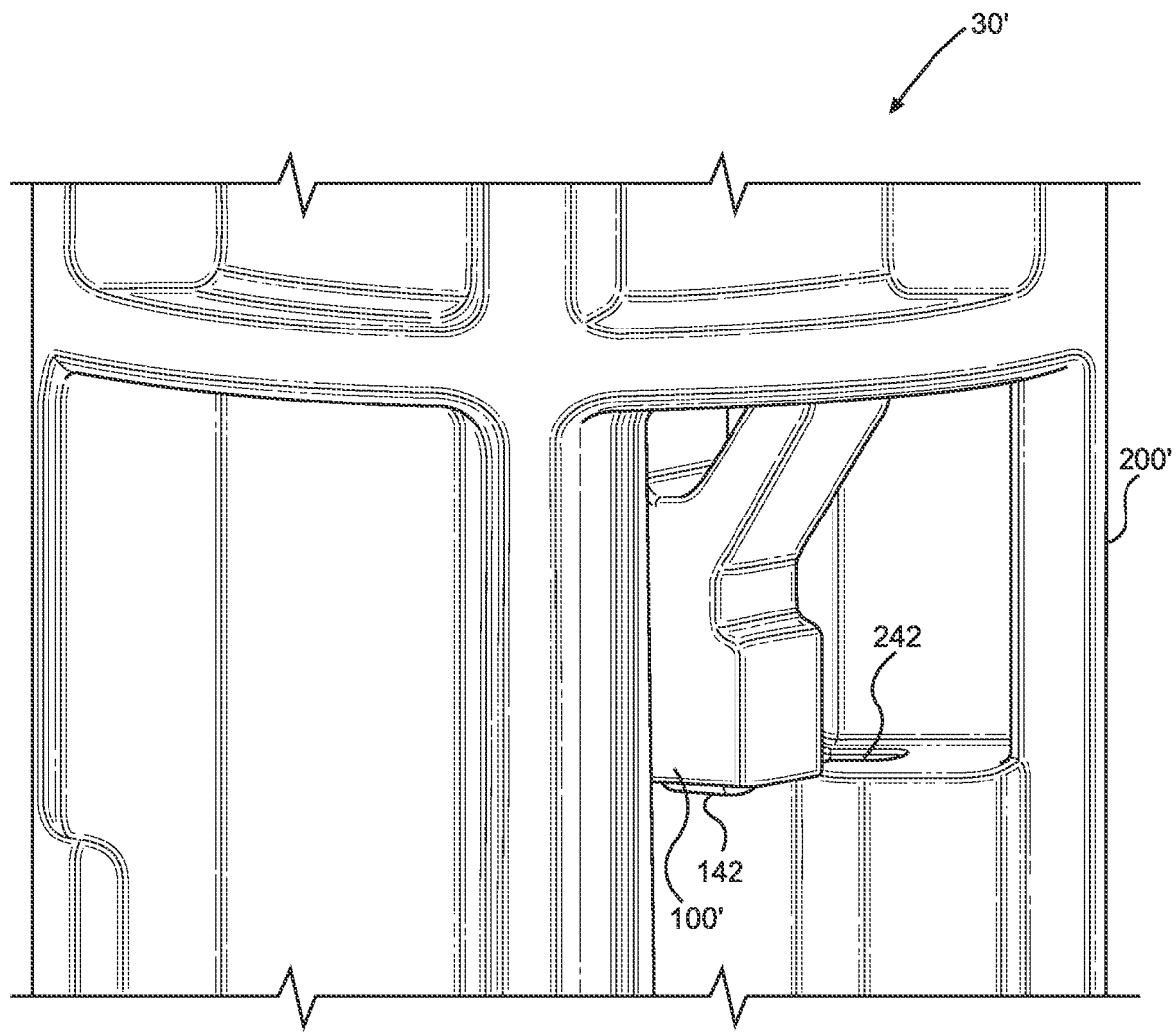
FIG. 23A illustrates a perspective view of a plunger rod according to another aspect of the disclosure shown in an unlocked configuration.
Figure 23B:
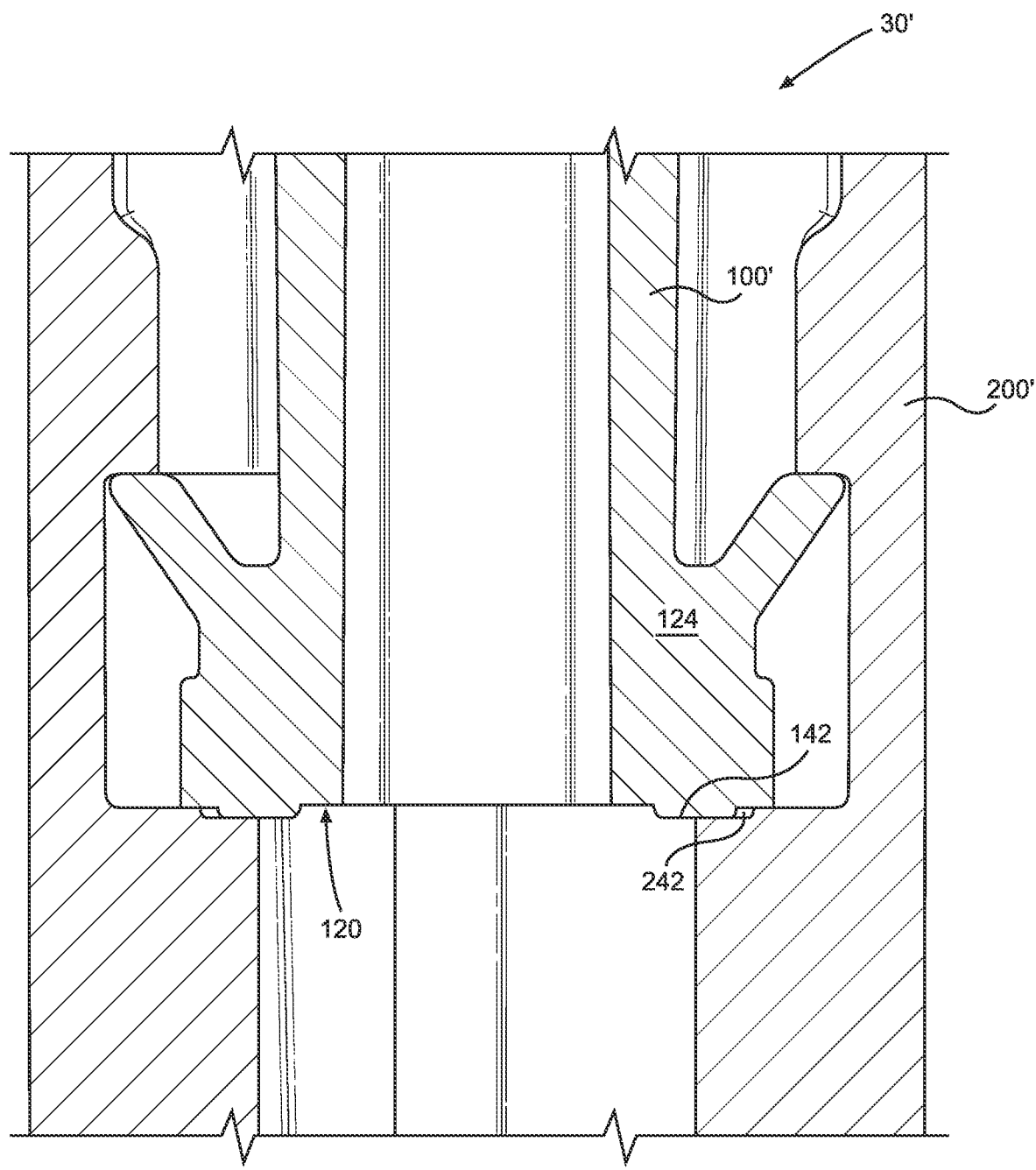
FIG. 23B illustrates a cross-sectional view of the plunger rod of FIG. 23A shown in a locked configuration.
Figure 23C:
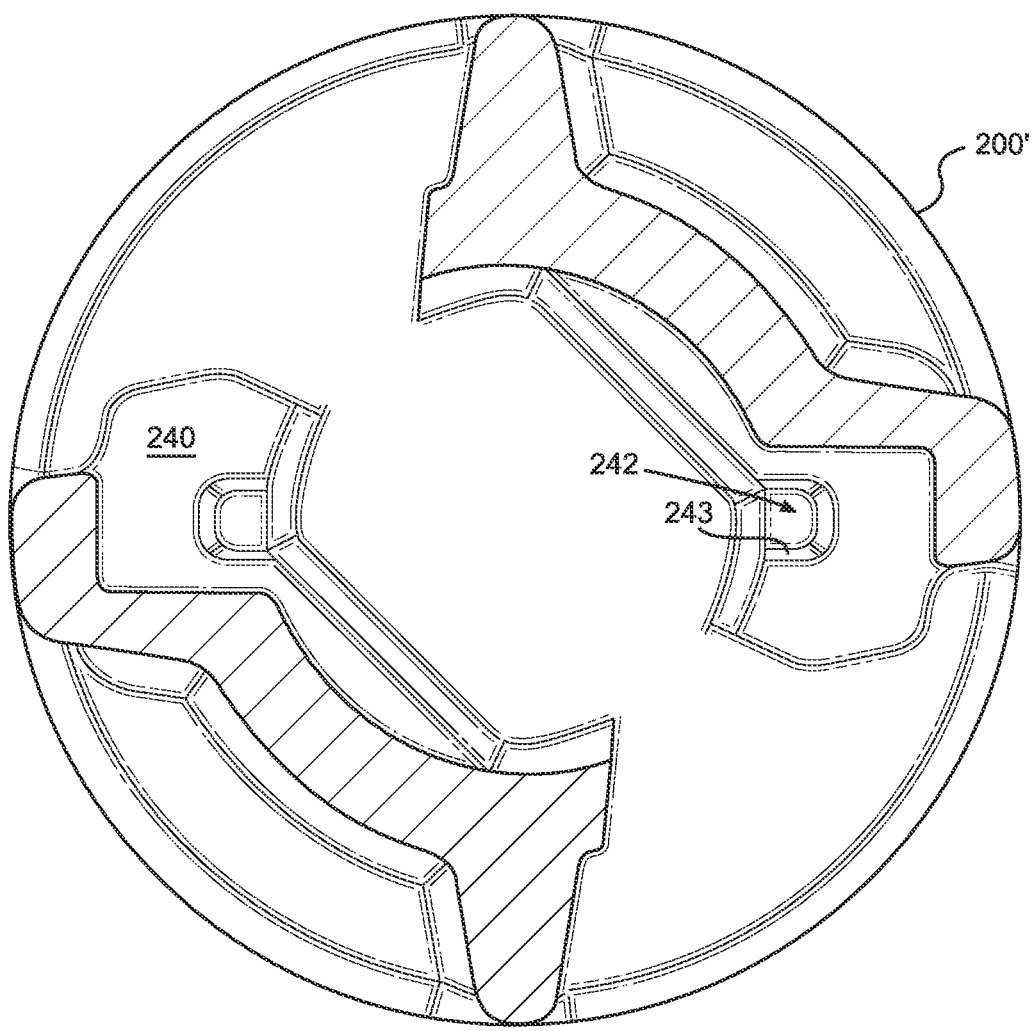
FIG. 23C illustrates a cross-sectional view of an outer housing according to another aspect of the disclosure.
Figure 23D:
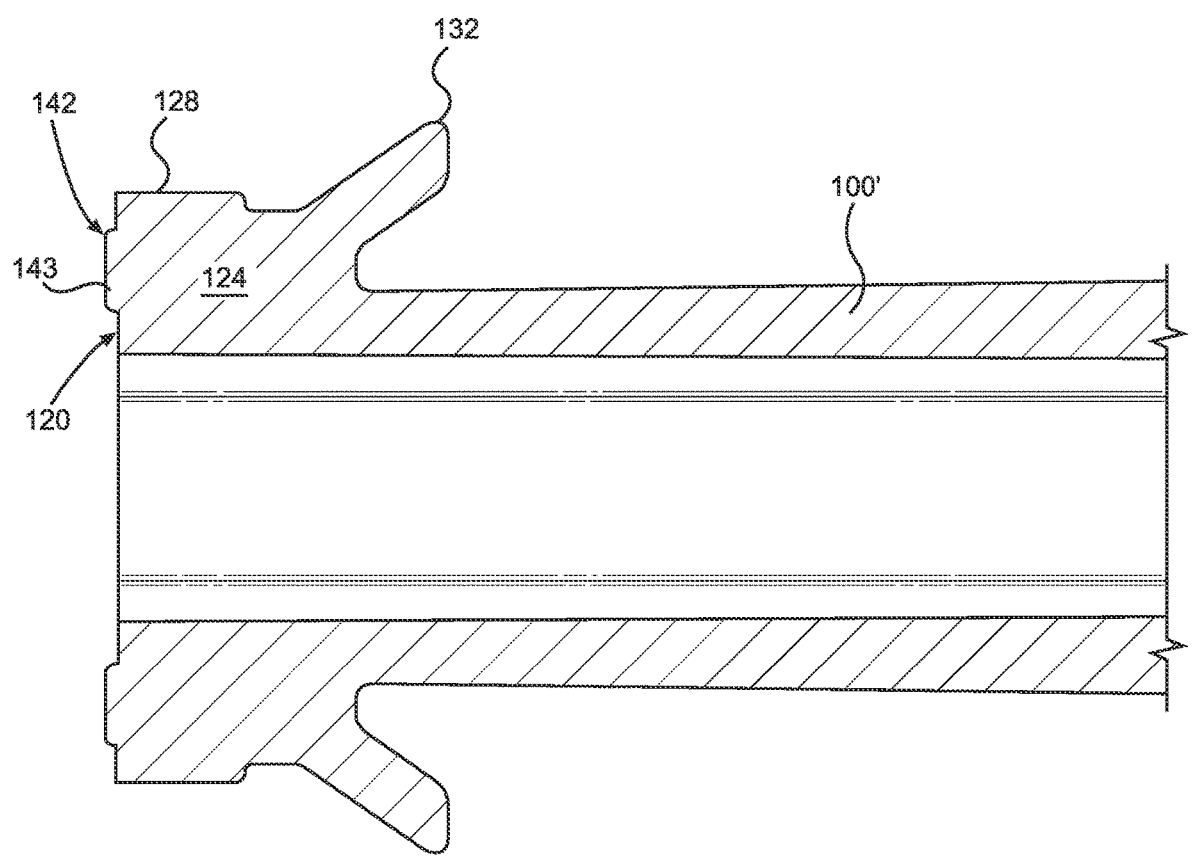
FIG. 23D illustrates a cross-sectional view of an inner body according to another aspect of the disclosure.

In some aspects, one or more additional retention features may be included on the outer housing 200 (e.g. on the lower and/or upper contact surfaces 240, 244) and/or on the inner body 100 (e.g. on the distal face 120) to prevent inadvertent rotation of the inner body 100 relative to the outer housing 200 that could transition the plunger rod 30 from the locked to the unlocked configuration. For example, referring to FIGS. 23A-23D, an embodiment of a plunger rod 30' is depicted having an inner body 100' and an outer housing 200'. Unless noted otherwise, features of the plunger rod 30', inner body 100', and outer housing 200' may be substantially similar to, or the same as, features described throughout this application with respect to the plunger rod 30, inner body 100, and outer housing 200, respectively, or other embodiments of plunger rods. FIGS. 23A-23C depict a notch 242 defined on the lower contact surface 240 of the outer housing 200'. The notch 242 is defined by at least one wall 243 extending from the lower contact surface 240 along the axial direction 2. The notch 242 extends, at least partly, distally along the axial direction 2 from the lower contact surface 240. A complementary protrusion 142 is defined on the inner body 100'. The protrusion 142 includes at least one wall 143 extending from the inner body 100' distally along the axial direction 2 (see FIG. 23D). In some aspects, the protrusion 142 may be defined adjacent the distal end 112 of the inner body 100'. In some aspects, the protrusion 142 may extend from the distal face 120. The protrusion 142 may be disposed on a portion of the distal face 120 that includes the base 128 of the retention member 124. When the plunger rod 30' is moved from the unlocked configuration to the locked configuration, the protrusion 142 is configured to be moved into the notch 242. When the protrusion 142 is in the notch 242, the inner body 100' and the outer housing 200' overlap axially at least via the axial overlap of the protrusion 142 and the notch 242. When the protrusion 142 is in the notch 242, the at least one wall 143 of the protrusion 142 may be configured to contact the at least one wall 243 of the notch 242. The contact between the walls 143 and 243 may prevent relative rotation between the inner body 100' and the outer housing 200'. Thus, when the plunger rod 30' is in the locked configuration, the engagement between the protrusion 142 and the notch 242 inhibits movement of the plunger rod 30' from the locked configuration to the unlocked configuration. FIG. 23A depicts the plunger rod 30' in an unlocked configuration, where the inner body 100' is rotationally arranged relative to the outer housing 200' such that the protrusion 142 is not within the notch 242. FIG. 23B depicts a cross-sectional view of the plunger rod 30' in a locked configuration, where the protrusion 142 on the inner body 100' is received in the notch 242 of the outer housing 200'. It will be understood that although FIGS. 23A-23D depict the notch 242 on the outer housing 200 and the complimentary protrusion 142 on the inner body 100, that this arrangement can be reversed, such that the protrusion 142 is disposed on the outer housing 200 while the notch 242 is disposed on the inner body 100. In some aspects, the plunger rod 30' may include multiple notches 242 and respective protrusions 142. In such aspects, all of the notches 242 may be disposed on the outer housing 200 while all the protrusions 142 may be disposed on the inner body 100. Alternatively, all of the notches 242 may be disposed on the inner body 100 while all the protrusions 142 may be disposed on the outer housing 200. Further alternatively, one or more notches 242 may be disposed on the outer housing 200 and one or more protrusions 142 may be disposed on the inner body 130, while another one or more of the other notches 242 may be disposed on the inner body 100 and another one or more protrusions 142 may be disposed on the outer housing 200.

The components described throughout this application can be manufactured from various materials and via various standard methods. In some aspects, the syringe assembly 10 and its components, for example the plunger rod 30 (including some or all of its components) can be formed via injection molding. In some aspects, the components described herein can include polypropylene. It will be appreciated that other materials are envisioned, and that this disclosure is not limited to a particular material or method of manufacture.

The liquid contained within the chamber of the syringe barrel can be aqueous, non-aqueous, or a combination of aqueous and non-aqueous liquids. In some embodiments, the liquid is a diluent intended for mixing with an active ingredient prior to administration to a subject. Exemplary diluents include, but are not limited to, water, 0.9% saline, 5% dextrose, Ringer's lactate solution, and other pharmaceutically acceptable diluents. In other embodiments, the liquid is a pharmaceutical formulation comprising an active ingredient and, optionally, one or more excipients. Thus, the invention provides a pharmaceutical product comprising a syringe assembly according to the present invention, wherein the liquid is a pharmaceutical formulation. Suitable excipients include, but are not limited to, a tonicity modifier, antioxidant, buffer, pH adjuster, preservative, solubilizer, stabilizer, or a combination of any of the forgoing. A diluent or pharmaceutical formulation can take on any suitable physical form including, but not limited to, solution, suspension, emulsion, or dispersion.

The active ingredient of the pharmaceutical formulation can be a therapeutic agent, a diagnostic agent, a nutrient, or a combination thereof. Examples of therapeutic agents include, but are not limited to antiinfectives, anesthetics, analgesics, anticoagulants, chemotherapeutics, hormones, antihypertensives, antiinflammatories, antiemetics, bronchodilators, adrenergics, immunoglobulins, antipsychotics, antidepressants, and combinations thereof. Examples of diagnostic agents include, but are not limited to x-ray, MRI and ultrasound contrast agents, cholecystokinetics, vasodilators, and combinations thereof. Examples of nutrients include, but are not limited to, salts, carbohydrates, minerals, vitamins, lipids, and combinations thereof.

In some embodiments, the active ingredient is a compound useful for pain management, muscle relaxation, sedation, and/or anesthesia. In certain embodiments, the active ingredient is an opioid, a benzodiazepine, beta blocker, or an α2-adrenergic receptor agonist. In particular embodiments, the active ingredient is morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, or a combination of the foregoing.

In other embodiments, the active ingredient is moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, hydroxyprogesterone, or a combination of the foregoing.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

What is claimed is:

1. A plunger rod for use with a syringe, the plunger rod comprising:
    an outer housing having a proximal end and a distal end opposite the proximal end, and further defining a lumen between the proximal end and the distal end; and
    an inner body configured to be movable within the lumen between a first position and a second position along an axial direction, the inner body comprising a retention member extending outward from the inner body in a direction angularly offset from the axial direction,
    wherein, when the inner body is in the first position relative to the outer housing, the plunger rod has a first length, and, when the inner body is in the second position relative to the outer housing, the plunger rod has a second length greater than the first length, and
    wherein, when the inner body is in the first position relative to the outer housing, the inner body is precluded from being rotated relative to the outer housing, and when the inner body is in the second position relative to the outer housing, the inner body is configured to be rotated relative to the outer housing until the retention member is received within a channel of the outer housing to preclude the inner body from moving relative to the outer housing in the axial direction.

2. The plunger rod of claim 1, wherein the outer housing defines a plurality of channels, including the channel, that are spaced along the axial direction, each of the plurality of channels being configured to receive the retention member.

3. The plunger rod of claim 2, wherein the plurality of channels include a distal channel, the channel is an intermediate channel adjacent the distal channel, and the retention member is configured to be received in the distal channel when the inner body is in the first position relative to the outer housing.

4. The plunger rod of claim 3, wherein the plurality of channels include a proximal channel spaced from the distal channel and the intermediate channel, the proximal channel configured to receive the retention member therein, and
    wherein, when the retention member is received in the proximal channel, the inner body is precluded from being rotated relative to the outer housing.

5. The plunger rod of claim 3, wherein the distal channel is tapered in the axial direction towards the distal end of the outer housing.

6. The plunger rod of claim 1, wherein the outer housing defines a contact surface in communication with the lumen, the contact surface contacting a face defined on the inner body after the inner body is rotated relative to the outer housing to the second position.

7. The plunger rod of claim 6, wherein the face of the inner body and the contact surface of the outer housing are in a friction fit when the face is in contact with the contact surface to resist relative rotation between the inner body and the outer housing.

8. The plunger rod of claim 6, wherein the contact surface includes a retention member contact surface and an inner body contact surface,
wherein the face of the inner body is defined by the distal end of the inner body and by the retention member, and
wherein the retention member contact surface is configured to contact the portion of the face defined by the retention member, and the inner body contact surface is configured to contact the portion of the face defined by the inner body that does not define the retention member.

9. The plunger rod of claim 8, wherein, when the inner body is in the second position, the inner body is configured to receive an axial force applied thereto and to transfer the axial force therefrom to the outer housing via the contact between the face of the inner body and the contact surface of the outer housing.

10. The plunger rod of claim 6, wherein the contact surface includes a lower contact surface and an upper contact surface spaced from the lower contact surface, wherein the retention member of the inner body is configured to be received into a space defined between the upper contact surface and the lower contact surface and to be in friction fit with the upper contact surface and the lower contact surface.

11. The plunger rod of claim 6, wherein one of the contact surface and the face of the inner body defines a notch thereon, and the other of the contact surface and the face defines a protrusion thereon, and
wherein, when the inner body is rotated relative to the outer housing while the inner body is in the second position, the protrusion is receivable in the notch.

12. The plunger rod of claim 11, wherein rotation of the inner body relative to the outer housing in a first rotational direction causes the protrusion to be moved into the notch, such that the protrusion is configured to contact at least one wall of the notch to preclude rotation of the inner body relative to the outer housing in a second rotational direction opposite the first rotational direction.

13. The plunger rod of claim 11, wherein the protrusion is disposed on the face, and the notch is disposed on the contact surface of the outer housing.

14. The plunger rod of claim 11, further comprising a plurality of the protrusions and a plurality of the notches, wherein the number of the plurality of the protrusions is the same as the number of the plurality of the notches.

15. The plunger rod of claim 1, wherein the retention member includes a base extending from the inner body and a resilient protrusion extending from the base,
wherein the resilient protrusion is configured to be deformed by application of a force, and resiliently undeforms upon removal of the force.

16. The plunger rod of claim 15, wherein the outer housing defines a detent extending into the lumen that is configured to be contacted by the retention member,
wherein, upon contact with the detent, the resilient protrusion is configured to deform due to the contact and due to application of the force, such that the retention member is moved past the detent, and
wherein the resilient protrusion resiliently returns to its original configuration when the resilient protrusion is moved past the detent to prevent separation of the inner body from the outer housing based on interaction between the resilient protrusion and the detent.

17. The plunger rod of claim 1, further comprising a plunger disposed adjacent to the distal end of the outer housing, such that the plunger is configured to contact a liquid within the syringe to cause dispensing thereof from the syringe.

18. A syringe assembly comprising:
a syringe configured to receive a liquid therein;
a plunger rod configured to be slidably received within the syringe, the plunger rod including:
an outer housing having a proximal end and a distal end opposite the proximal end, and further defining a lumen between the proximal end and the distal end; and
an inner body configured to be movable within the lumen between a first position and a second position along an axial direction, the inner body comprising a retention member extending outward from the inner body in a direction angularly offset from the axial direction; and
a plunger disposed on the outer housing,
wherein, when the inner body is in the first position relative to the outer housing, the plunger rod has a first length, and, when the inner body is in the second position relative to the outer housing, the plunger rod has a second length greater than the first length, and
wherein, when the inner body is in the first position relative to the outer housing, wherein, when the inner body is in the first position relative to the outer housing, the inner body is precluded from being rotated relative to the outer housing, and when the inner body is in the second position relative to the outer housing, the inner body is configured to be rotated relative to the outer housing until the retention member is received within a channel of the outer housing to preclude the inner body from moving relative to the outer housing in the axial direction.

19. The syringe assembly of claim 18, wherein the liquid comprises an active ingredient, the active ingredient comprising at least one of a therapeutic agent, a diagnostic agent, or a nutrient.

20. The syringe assembly of claim 19, wherein the active ingredient is selected from the group consisting of an opioid, benzodiazepine, α2-adrenergic receptor agonist, beta blocker, morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, and hydroxyprogesterone.

21. A method of dispensing of a liquid from a syringe barrel using a plunger rod having an outer housing and an inner body receivable within the outer housing, the plunger rod having a proximal end and a distal end spaced from the proximal end along an axial direction, the method comprising:
    moving the inner body relative to the outer housing in the axial direction from a first position to a second position away from the proximal end to expand the plunger rod to an extended configuration, wherein the inner body is precluded from being rotated relative to the outer housing while being moved in the axial direction from the first position to the second position;
    rotating the inner body relative to the outer housing to prevent axial movement of the inner body relative to the outer housing when the inner body is in the second position; and
    applying an axial force to the inner body to cause the plunger rod to move relative to the syringe barrel.

22. The method of claim 21, wherein the plunger rod has a first length measured between the proximal end and the distal end when the inner body is in the first position, and a second length greater than the first length measured between the proximal end and the distal end when the inner body is in the second position.

23. The method of claim 21, wherein the outer housing includes a contact surface, and the inner body includes a face, and wherein rotating the inner body relative to the outer housing when the inner body is in the second position includes axially aligning the contact surface with the face such that the contact surface and the face to contact each other to prevent axial movement of the inner body relative to the outer housing.

24. The method of claim 21, further comprising inserting the plunger rod into the syringe barrel, such that the plunger rod is configured to be slidably moved within the syringe barrel.

25. The method of claim 21, further comprising, prior to expanding the plunger rod to the extended configuration, inserting the inner body into the outer housing, wherein the inner body is precluded from being rotated relative to the outer housing while being moved into the outer housing.

26. The plunger rod of claim 4, wherein the first position is the distal most position of the inner body within the lumen of the outer housing.

27. The plunger rod of claim 4, wherein the distal channel and the proximal channel are circumferentially offset.

* * * * *